(12) United States Patent
Kusukame et al.

(10) Patent No.: US 11,045,127 B2
(45) Date of Patent: *Jun. 29, 2021

(54) METHOD FOR PREDICTING AROUSAL LEVEL AND AROUSAL LEVEL PREDICTION APPARATUS

(71) Applicant: PANASONIC INTELLECTUAL PROPERTY CORPORATION OF AMERICA, Torrance, CA (US)

(72) Inventors: Koichi Kusukame, Nara (JP); Shinichi Shikii, Nara (JP); Kazuki Funase, Osaka (JP)

(73) Assignees: PANASONIC INTELLECTUAL PROPERTY, Torrance, CA (US); CORPORATION OF AMERICA, Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,202

(22) Filed: Jun. 5, 2020

(65) Prior Publication Data

US 2020/0330047 A1    Oct. 22, 2020

Related U.S. Application Data

(63) Continuation of application No. 16/439,257, filed on Jun. 12, 2019, now Pat. No. 10,716,502, which is a (Continued)

(30) Foreign Application Priority Data

Jan. 15, 2016    (JP) .................................. 2016-006681

(51) Int. Cl.
*A61B 5/18* (2006.01)
*G08B 21/06* (2006.01)
(Continued)

(52) U.S. Cl.
CPC .................. *A61B 5/18* (2013.01); *A61B 5/01* (2013.01); *A61B 5/024* (2013.01); *A61B 5/026* (2013.01);
(Continued)

(58) Field of Classification Search
CPC .. A61B 5/18; A61B 5/01; A61B 5/024; A61B 5/026; A61B 5/0816; A61B 5/486;
(Continued)

(56) References Cited

U.S. PATENT DOCUMENTS 6,419,629 B1    7/2002    Balkin
8,576,081 B2    11/2013    Hatakeyama
(Continued)

FOREIGN PATENT DOCUMENTS

CN    104973054    10/2015
JP    8-188124    7/1996
(Continued)

OTHER PUBLICATIONS

English Translation of Chinese Search Report dated Mar. 5, 2020 for the related Chinese Patent Application No. 201610523463.5.

*Primary Examiner* — John A Tweel, Jr.
(74) *Attorney, Agent, or Firm* — Greenblum & Bernstein, P.L.C.

(57) ABSTRACT

A method for predicting an arousal level used by a computer of an arousal level prediction apparatus that predicts an arousal level of a user is provided. The method includes obtaining current biological information regarding the user detected by a sensor, and calculating a current arousal level of the user based on the current biological information. The method further includes obtaining current environment information indicating a current environment around the user, and predicting a future arousal level, which is an arousal level a certain period of time later, based on the
(Continued)

current arousal level and the current environment information. Based on the predicted future arousal level, the method further issues a notification to the user, or controls an operation of a device.

21 Claims, 9 Drawing Sheets

Related U.S. Application Data continuation of application No. 15/203,627, filed on Jul. 6, 2016, now Pat. No. 10,362,980.

(60) Provisional application No. 62/195,355, filed on Jul. 22, 2015.

(51) Int. Cl.

| | | |
|---|---|---|
| *B60K 28/06* | (2006.01) | |
| *A61B 5/00* | (2006.01) | |
| *A61B 5/026* | (2006.01) | |
| *B60H 1/00* | (2006.01) | |
| *A61B 5/08* | (2006.01) | |
| *A61B 5/01* | (2006.01) | |
| *G16H 40/63* | (2018.01) | |
| *A61B 5/024* | (2006.01) | |
| *G16H 40/67* | (2018.01) | |
| *G16H 50/50* | (2018.01) | |
| *G16H 50/30* | (2018.01) | |
| *G16H 50/20* | (2018.01) | |
| *A61B 5/0295* | (2006.01) | |
| *A61B 5/087* | (2006.01) | |
| *A61B 5/11* | (2006.01) | |
| *A61B 5/1455* | (2006.01) | |
| *A61B 5/16* | (2006.01) | |
| *A61M 21/00* | (2006.01) | |
| *G06F 3/16* | (2006.01) | |
| *A61B 3/113* | (2006.01) | |
| *A61B 5/103* | (2006.01) | |
| *A61B 5/091* | (2006.01) | |
| *A61B 5/0285* | (2006.01) | |
| *G04F 10/00* | (2006.01) | |

(52) U.S. Cl.
CPC ........ *A61B 5/0295* (2013.01); *A61B 5/02405* (2013.01); *A61B 5/02444* (2013.01); *A61B 5/0816* (2013.01); *A61B 5/0878* (2013.01); *A61B 5/1118* (2013.01); *A61B 5/14551* (2013.01); *A61B 5/165* (2013.01); *A61B 5/486* (2013.01); *A61B 5/4806* (2013.01); *A61B 5/7275* (2013.01); *A61M 21/00* (2013.01); *B60H 1/00742* (2013.01); *B60K 28/06* (2013.01); *G06F 3/165* (2013.01); *G08B 21/06* (2013.01); *G16H 40/63* (2018.01); *G16H 40/67* (2018.01); *G16H 50/20* (2018.01); *G16H 50/30* (2018.01); *G16H 50/50* (2018.01); *A61B 3/113* (2013.01); *A61B 5/0261* (2013.01); *A61B 5/0285* (2013.01); *A61B 5/02416* (2013.01); *A61B 5/091* (2013.01); *A61B 5/1032* (2013.01); *A61B 5/7278* (2013.01); *A61B 2503/22* (2013.01); *A61B 2503/24* (2013.01); *A61B 2560/0242* (2013.01); *A61M 2021/0027* (2013.01); *A61M 2021/0044* (2013.01); *A61M 2021/0066* (2013.01); *A61M 2021/0083* (2013.01); *A61M 2205/3303* (2013.01); *B60K 2370/193* (2019.05); *G04F 10/00* (2013.01)

(58) Field of Classification Search
CPC ........ G16H 50/30; G06F 3/165; B60K 28/06; B60K 2370/193; G08B 21/06
USPC .......................................................... 600/28
See application file for complete search history.

(56) References Cited

U.S. PATENT DOCUMENTS

| | | | |
|---|---|---|---|
| 8,730,326 B2 | 5/2014 | Terada | |
| 8,847,771 B2 | 9/2014 | Gunaratne | |
| 8,948,861 B2 | 2/2015 | Rai | |
| 9,702,712 B2 * | 7/2017 | Kitagawa | G01C 21/3407 |
| 9,848,813 B2 | 12/2017 | Kronberg | |
| 10,076,273 B2 | 9/2018 | Berckmans | |
| 10,227,063 B2 | 3/2019 | Abreu | |
| 10,362,980 B2 | 7/2019 | Kusukame | |
| 10,716,502 B2 * | 7/2020 | Kusukame | A61B 5/165 |
| 2003/0043045 A1 | 3/2003 | Yasushi et al. | |
| 2006/0224047 A1 | 10/2006 | Suzuki et al. | |
| 2015/0080756 A1 | 3/2015 | Robinson | |
| 2015/0285653 A1 | 10/2015 | Kim et al. | |
| 2015/0363657 A1 | 12/2015 | Shigemura | |

FOREIGN PATENT DOCUMENTS

| | | |
|---|---|---|
| JP | 2003-061939 | 3/2003 |
| JP | 2004-318266 | 11/2004 |
| JP | 2005-337607 | 12/2005 |
| JP | 2006-271897 | 10/2006 |
| JP | 2007-094542 | 4/2007 |
| JP | 2007-203913 | 8/2007 |
| JP | 2008-006007 | 1/2008 |
| JP | 2008-065776 | 3/2008 |
| JP | 2008-073450 | 4/2008 |
| JP | 2008-188108 | 8/2008 |
| JP | 2009-048605 | 3/2009 |
| JP | 2009-202841 | 9/2009 |
| JP | 2009-213768 | 9/2009 |
| JP | 2010-122732 | 6/2010 |
| JP | 2011-065561 | 3/2011 |
| JP | 2012-118951 | 6/2012 |
| JP | 2013-027570 | 2/2013 |
| JP | 2013-123524 | 6/2013 |
| JP | 2013-172899 | 9/2013 |
| JP | 03192066 | 7/2014 |
| JP | 2014-144096 | 8/2014 |
| JP | 2015-012948 | 1/2015 |
| JP | 2015-018517 | 1/2015 |
| WO | 2014/027933 A1 | 2/2014 |

* cited by examiner

METHOD FOR PREDICTING AROUSAL LEVEL AND AROUSAL LEVEL PREDICTION APPARATUS

CROSS-REFERENCE TO RELATED APPLICATIONS

This application is a continuation of U.S. patent application Ser. No. 16/439,257, filed on Jun. 12, 2019, which is a continuation of U.S. patent application Ser. No. 15/203,627, filed on Jul. 6, 2016 and now U.S. Pat. No. 10,362,980 issued on Jul. 30, 2019, which claims priority to Japanese Application No. 2016-006681, filed on Jan. 15, 2016, and U.S. Provisional Patent Application No. 62/195,355, filed Jul. 22, 2015. The disclosure of each of these documents, including the specification, drawings, and claims, is incorporated herein by reference in its entirety.

BACKGROUND

1. Technical Field

The present disclosure relates to a method for predicting an arousal level and an arousal level prediction apparatus.

2. Description of the Related Art

A system that obtains biological information regarding a user and that calculates an arousal level of the user from the obtained biological information has been proposed (e.g., refer to Japanese Unexamined Patent Application Publication No. 2013-123524 and Japanese Unexamined Patent Application Publication No. 2009-48605). The arousal level indicates a degree of arousal, and a low arousal level indicates that the user is feeling drowsy.

In Japanese Unexamined Patent Application Publication No. 2013-123524, a method for determining an arousal level from a heartbeat signal obtained as biological information is disclosed. In Japanese Unexamined Patent Application Publication No. 2009-48605, a vehicle system is disclosed that avoids a drivers falling asleep at a wheel by outputting an alarm sound for the driver if a current arousal level falls below a certain threshold.

SUMMARY

In one general aspect, the techniques disclosed here feature a method for predicting an arousal level used by a computer of an arousal level prediction apparatus that predicts an arousal level of a user. The method includes obtaining current biological information regarding the user detected by a first sensor, calculating a current arousal level of the user on the basis of the current biological information, obtaining current environment information indicating a current environment around the user detected by a second sensor, predicting a future arousal level, which is an arousal level a certain period of time later, on the basis of the current arousal level and the current environment information, and (i) issuing a notification to the user or (ii) controlling another device, on the basis of the future arousal level.

According to the present disclosure, a method for predicting an arousal level and an arousal level prediction apparatus capable of predicting a decrease in an arousal level of the user are provided.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
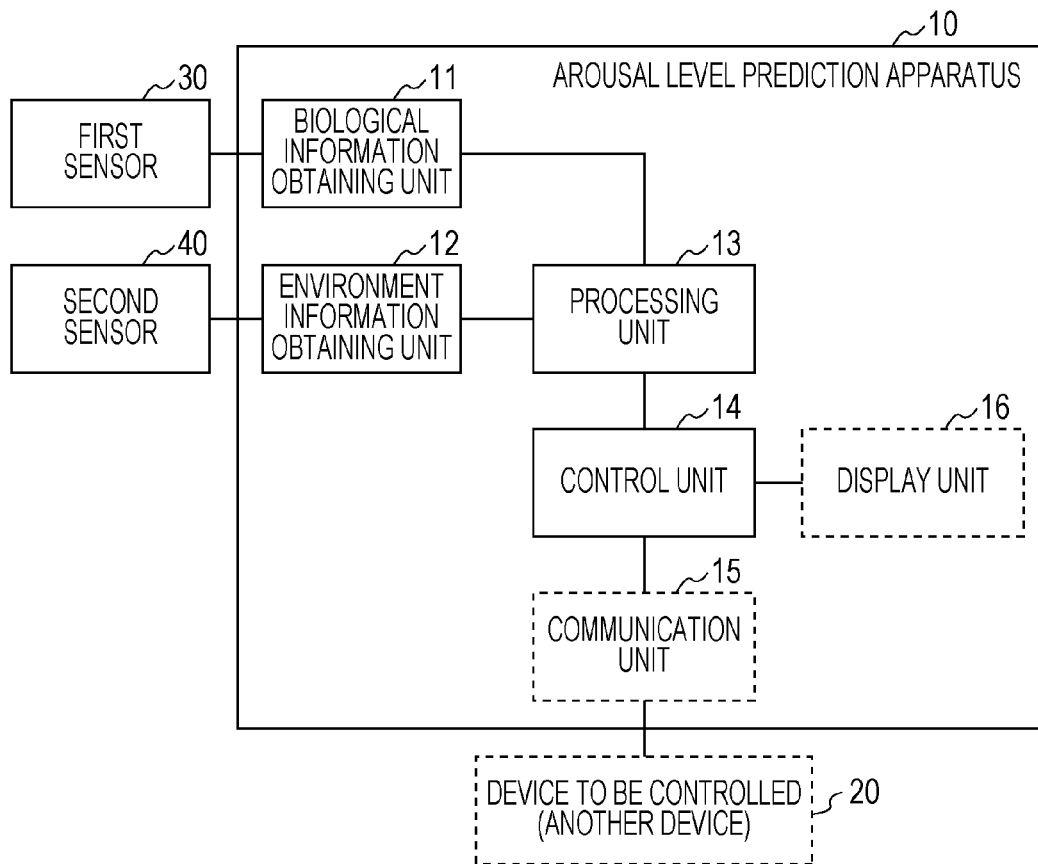
FIG. 1 is a block diagram illustrating an example of the configuration of an arousal level prediction apparatus according to a first embodiment.

Underlying Knowledge Forming Basis of the Present Disclosure

The present inventors has noticed that, in the examples of the related art, an arousal level of the user is undesirably increased after the arousal level of the user falls below a certain threshold. Once the arousal level of the user falls below the certain threshold, a strong stimulus is needed to increase the arousal level (arouse the user). If a strong stimulus is given to the user during driving, for example, the user might be surprised, which might affect the driving operation.

The present disclosure is established in order to solve the above problem and provides a method for predicting an arousal level and an arousal level prediction apparatus capable of predicting a decrease in the arousal level of the user.

A method for predicting an arousal level according to an aspect of the present disclosure is a method for predicting an arousal level used by a computer of an arousal level prediction apparatus that predicts an arousal level of a user. The method includes obtaining current biological information regarding the user detected by a first sensor, calculating a current arousal level of the user on the basis of the current biological information, obtaining current environment information indicating a current environment around the user detected by a second sensor, predicting a future arousal level, which is an arousal level a certain period of time later, on the basis of the current arousal level and the current environment information, and (i) issuing a notification to the user or (ii) controlling another device, on the basis of the future arousal level.

According to this aspect, since the future arousal level can be predicted, a decrease in the arousal level of the user can be predicted. As a result, a strong stimulus is not needed to increase the arousal level, and a decrease in the arousal level of the user can be suppressed with a mild stimulus.

Here, for example, in the predicting a future arousal level, a rate of decrease in the arousal level may be estimated on the basis of how likely it is for a person to become drowsy indicated by the current environment information. The future arousal level may be predicted by correcting the current arousal level to the arousal level the certain period of time later using the rate of decrease.

In addition, for example, the issuing or the controlling may be performed only if the future arousal level is lower than a certain threshold.

In addition, for example, the arousal level prediction apparatus may be mounted on an automobile. The certain period of time may be included in a time taken to arrive at a destination input by the user to a navigation system installed in the automobile.

Here, for example, the biological information may include information indicating a heart rate. The current arousal level may become lower as a current heart rate of the user becomes lower.

In addition, for example, the first sensor may detect the current heart rate of the user using any of a milliwave sensor, a pulse oximeter, a speckle camera, and a laser Doppler velocimeter.

In addition, for example, the first sensor may include a camera or a milliwave sensor and detect a current respiratory rate of the user by measuring movement of a surface of the user's body.

In addition, for example, the biological information may include information indicating a respiratory rate or an amount of air breathed. The current arousal level may become lower as a current respiratory rate of the user becomes lower or a current amount of air breathed by the user becomes smaller.

In addition, for example, the first sensor may detect the current heart rate of the user by measuring a change in a color of the user's skin using a photodiode.

In addition, for example, the first sensor may detect the current respiratory rate of the user by measuring a change in a color of the user's skin using a photodiode.

In addition, for example, the first sensor may detect the current respiratory rate of the user, duration of each breath, or the current amount of air breathed by the user by measuring a current temperature of the user's lips or a portion under the user's nose using a radiation thermometer.

In addition, for example, the biological information may include information indicating a body surface temperature of a periphery of a person's body and a deep-body temperature. The current arousal level may become lower as a current body surface temperature of a periphery of the user's body becomes closer to the deep-body temperature.

Here, the deep-body temperature may be estimated on the basis of a temperature of the user's forehead, and the temperature of the periphery may be estimated on the basis of a temperature of the user's nose or hands or another body part.

In addition, for example, the biological information may include information indicating a blood flow volume in a periphery of a person's body. The current arousal level may become lower as a current blood flow volume in a periphery of the user's body becomes larger.

In addition, for example, the first sensor may detect the current blood flow volume in the periphery of the user's body by measuring blood flow distribution of the user using a laser speckle camera.

In addition, for example, the first sensor may calculate pulse wave velocity on the basis of a time difference in a change in blood flow volume between an artery of a measured body part of the user and a vein in the periphery by measuring the change in the blood flow volume in the artery of the measured body part of the user and the vein in the periphery using a laser speckle camera or a camera.

In addition, for example, the biological information may include information indicating the pulse wave velocity or blood pressure. The current arousal level may become lower as the blood pressure or the pulse wave velocity indicated by the information included in the biological information becomes lower.

In addition, for example, the current environment information may include information indicating a current illumination around the user. The rate of decrease in the arousal level may become higher as the current illumination becomes lower.

In addition, for example, the current environment information may include information indicating a current wind speed around the user. A higher rate of decrease in the arousal level may be estimated as the current wind speed becomes lower.

In addition, for example, the method may further include obtaining sleep information indicating hours of sleep of the user of a previous day and predicting the future arousal level on the basis of the current arousal level, the current environment information, and the sleep information.

In addition, for example, the method may further include obtaining past sleep information indicating hours of sleep of the user in a certain period of time in past and predicting the future arousal level on the basis of the current arousal level, the current environment information, and the past sleep information.

In addition, for example, the method may further include obtaining information indicating an activity history of the user and predicting the future arousal level on the basis of the current arousal level, the current environment information, and the activity history.

In addition, for example, the other device may be an air conditioner installed in the same space in which the arousal level prediction apparatus is installed. Setting temperature or air volume of the air conditioner may be changed if the future arousal level is lower than a certain threshold.

In addition, for example, the other device may be a lighting device installed in the same space in which the arousal level prediction apparatus is installed. Brightness of the lighting device may be increased if the future arousal level is lower than a certain threshold.

In addition, for example, the other device may be a personal computer including a display used by the user. A color or luminance of the display of the personal computer may be changed if the future arousal level is lower than a certain threshold.

In addition, an arousal level prediction apparatus according to an aspect of the present disclosure is an arousal level prediction apparatus including a first sensor that detects biological information, a second sensor that detects environment information indicating an environment around a user, a processor that calculates a current arousal level of the user on the basis of current biological information regarding the user detected by the first sensor and that predicts a future arousal level, which is an arousal level a certain period of time later, on the basis of the current arousal level and current environment information detected by the second sensor, and a controller that (i) issues a notification to the user or (ii) controls another device, on the basis of the future arousal level.

It should be noted that these general or specific embodiments may be implemented as a system, a method, an integrated circuit, a computer program, a storage medium such as a computer-readable CD-ROM, or any selective combination thereof.

A method for predicting an arousal level according to each of embodiments of the present disclosure will be specifically described hereinafter with reference to the drawings. The following embodiments are specific examples of the present disclosure. Values, shapes, materials, components, positions at which the components are arranged, and the like described in the following embodiments are examples, and do not limit the present disclosure. Among the components described in the following embodiments, ones not described in the independent claims, which define broadest concepts, will be described as arbitrary components.

First Embodiment

Configuration of Arousal Level Prediction Apparatus

FIG. 1 is a block diagram illustrating the configuration of an arousal level prediction apparatus 10 according to a first embodiment.

As illustrated in FIG. 1, the arousal level prediction apparatus 10 includes a biological information obtaining unit 11, an environment information obtaining unit 12, a processing unit 13, a control unit 14, a communication unit 15, and a display unit 16 and predicts an arousal level of a user. The arousal level prediction apparatus 10 is a computer or the like. A first sensor 30 detects biological information, and a second sensor 40 detects environment information indicating an environment around the user.

Biological Information Obtaining Unit 11

The biological information obtaining unit 11 obtains current biological information regarding the user detected by the first sensor 30. In the present embodiment, the biological information obtaining unit 11 obtains the current biological information by communicating with the first sensor 30 directly or through the communication unit 15. The biological information may be information indicating a heart rate, variation in a heartbeat period, a respiratory rate, the amount of air breathed, blink speed, the stability of respiration periods, facial expressions, movements of the user's eyes, body surface temperature distribution, body surface temperature, deep-body temperature, blood flow distribution inside the user's body, or any combination of these pieces of information. The first sensor 30, which detects biological information, may be a heart rate (pulse) sensor, a respiration sensor, a thermal image sensor, or a blood flow sensor, or may be any combination of these sensors. Alternatively, the first sensor 30, which detects biological information, may be any combination of a milliwave sensor, a pulse oximeter, a speckle camera, a laser Doppler velocimeter, a photodiode, a radiation thermometer, a camera, a time-of-flight (TOF) sensor, a microphone attached to the user's clothes, a thermal image sensor, and a laser speckle camera.

Specific exemplary combinations of the biological information and the first sensor 30 will be described hereinafter.

When Biological Information Includes Information Indicating Heart Rate

For example, the biological information may include information indicating the heart rate, and a current arousal level may become lower as a current heart rate becomes lower. This is because it is known that a person tends to feel drowsy when the heart rate is low. The first sensor 30 in this case is a heart rate sensor.

The first sensor 30 may detect the current heart rate of the user as biological information using any of, for example, a milliwave sensor, a pulse oximeter, a speckle camera, and a laser Doppler velocimeter as the heart rate sensor. The biological information obtaining unit 11 may calculate, from a signal indicating the heart rate obtained from the first sensor 30, a ratio of a low-frequency (LF) component (0.04 to 0.15 Hz) to a high-frequency (HF) component (0.15 to 0.4 Hz) and obtain the ratio as biological information. This is because it is known that the HF component decreases when a person is active and increases when the person is not active. The ratio may be used by the processing unit 13, which will be described later, to accurately calculate the current arousal level of the user.

When Biological Information Includes Information Indicating Respiratory Rate or Amount of Air Breathed Alternatively, for example, the biological information may include information indicating the respiratory rate or the amount of air breathed, and the current arousal level may become lower as a current respiratory rate or a current amount of air breathed becomes lower. This is because it is known that a person tends to feel drowsy when the respiratory rate is low or the amount of air breathed is small. The first sensor 30 in this case is a respiration sensor.

The first sensor 30 may detect the current respiratory rate of the user using, for example, a milliwave sensor that measures the movement of the user's chest using millimeter waves. Alternatively, the first sensor 30 may detect the current respiratory rate of the user, for example, by analyzing temporal changes in an image of the user's chest captured using a camera and measuring the movement of the user's chest. This is because the movement of the chest and respiration are related to each other. Although the first sensor 30 measures the user's chest, a body part measured by the first sensor 30 is not limited to this. The first sensor 30 may measure the movement of a surface of any body part related to respiration in order to detect the current respiratory rate of the user.

Alternatively, the first sensor 30 may detect the current heart rate of the user, for example, by measuring a change in a color of the user's skin using a photodiode. The first sensor 30 can calculate the heart rate of the user because the user's skin reddens when peripheral blood flow volume increases and the peripheral blood flow volume changes in accordance with the heart rate.

Alternatively, the first sensor 30 may detect the current respiratory rate of the user, for example, by measuring a change in the color of the user's skin using a photodiode. The first sensor 30 can calculate the respiratory rate of the user by measuring the color of the user's skin using a photodiode or the like because oxygen saturation of the user changes due to respiration and accordingly the color of the user's skin slightly changes.

The heart rate can be calculated on the basis of a color change of 0.5 to 3 Hz, and the respiratory rate can be calculated, for example, on the basis of an average color (temperature) in a minute.

In addition, because variation in heartbeat changes due to respiration, the respiratory rate may be calculated on the basis of a change in the variation in heartbeat.

Alternatively, the first sensor 30 may detect the current respiratory rate, the duration of each breath, or the current amount of air breathed of the user by measuring a current temperature of the user's lips or a portion under the user's nose using a radiation thermometer. This is because the temperature of a person's lips or the portion under the person's nose decreases when the person breathes in and increases when the person breathes out (exhaled air is hotter than ambient air). By measuring the current temperature of the user's lips or the portion under the user's nose using a radiation thermometer, therefore, the respiratory rate, the duration of each breath, or the amount of air breathed can be detected. Alternatively, the first sensor 30 may calculate the amount of air breathed on the basis of a difference between the temperature of the user's lips or the portion under the user's nose when the user breathes in and the temperature of the user's lips or the portion under the user's nose when the user breathes out using a radiation thermometer. This method, in which the first sensor 30 detects the current respiratory rate of the user or the current amount of air breathed by the user using a radiation thermometer, is the cheapest noncontact method.

Alternatively, the first sensor 30 may detect the current respiratory rate of the user or the amount of air breathed by the user using a speckle camera or a laser Doppler velocimeter. By measuring a flow of air exhaled from the user's nose or mouth using a speckle camera or a laser Doppler velocimeter, the respiratory rate or the amount of air breathed can be calculated. This method, in which the first sensor 30 detects the current respiratory rate of the user or the current amount of air breathed by the user using a speckle camera or a laser Doppler velocimeter, is expensive, but the current respiratory rate of the user or the current amount of air breathed by the user can be detected most accurately.

Alternatively, the first sensor 30 may detect the current respiratory rate of the user or the current amount of air breathed by the user by detecting a sound of the user's breathing using a microphone or a piezoelectric sensor attached to the user's clothes, a seat, or a seatbelt. By incorporating a microphone into an earphone or a portion of glasses in contact with the user's skin, for example, the sound of the user's breathing can be detected. This is because the first sensor 30 can detect the respiratory rate by measuring the sound of the user's breathing detected by the microphone and the amount of air breathed on the basis of the pitch and length of the sound of the user's breathing detected by the microphone. This method, in which the first sensor 30 detects the current respiratory rate of the user or the current amount of air breathed by the user in the above-described manner, is the cheapest contact method.

Alternatively, the first sensor 30 may detect the current respiratory rate of the user or the current amount of air breathed by the user by measuring the movement of the user's chest using a camera and a TOF sensor. This method for detecting the current respiratory rate of the user or the current amount of air breathed by the user is advantageous in that the method is a noncontact method and can also be used for measuring heartbeat.

The first sensor 30 that is a respiration sensor may detect only the respiratory rate or the amount of air breathed, or may detect both the respiratory rate and the amount of air breathed. In the latter case, the first sensor 30 can be used by the processing unit 13, which will be described later, to accurately calculate the current arousal level of the user.

When Biological Information Includes Information Indicating Body Surface Temperature and Deep-Body Temperature Alternatively, for example, the biological information may include information indicating the body surface temperature and the deep-body temperature of a periphery of a person's body, and the current arousal level may become lower as a current body surface temperature of the periphery of the user's body becomes closer to the deep-body temperature. This is because it is known that a person tends to feel drowsy when the temperature of the periphery, which includes the nose, the hands, and the feet, becomes closer to the deep-body temperature. The deep-body temperature can be measured, for example, by measuring the temperature of the forehead, a side of the neck (where an artery exists), an armpit, or the like.

The first sensor 30 may be a thermal image sensor, which is used for detecting the current body surface temperature and the deep-body temperature of the periphery of the user's body. Alternatively, the first sensor 30 may measure the body surface temperature distribution of the user, for example, using a thermopile or a bolometer. This is because, in this case, the deep-body temperature can be estimated on the basis of body surface temperatures of a plurality of body parts and ambient temperature. More specifically, this is because it is known that a difference (first difference) between the deep-body temperature and the temperature of the forehead, a difference (second difference) between the temperature of the forehead and the temperature of the hands, and a difference (third difference) between the temperature of the hands and ambient temperature have a certain correlation. That is, the first difference can be estimated by calculating the second difference and the third difference, and the deep-body temperature can be estimated from the first temperature and the temperature of the forehead. If ambient temperature and humidity are known, the processing unit 13, which will be described later, can estimate the sensible temperature of a person on the basis of the ambient temperature and the humidity. In this case, whether an increase in the temperature of the periphery of the user's body is caused by external heat or drowsiness can be determined, thereby making it possible to estimate the arousal level more accurately.

When Biological Information Includes Information Indicating Blood Flow Volume

Alternatively, for example, the biological information may include information indicating the blood flow volume of the periphery of a person, and the current arousal level may become lower as a current blood flow volume of the periphery of the user's body becomes larger. This is because it is known that a person tends to feel drowsy when the blood flow volume of the periphery of the person's body is large. The first sensor 30 in this case may be a blood flow sensor.

The first sensor 30 may detect the blood flow volume of the periphery of the user's body by measuring the blood flow distribution of the user using a laser speckle camera as the blood flow sensor. This is because the blood flow distribution can be measured on the basis of variation in interference fringes of laser light.

Alternatively, for example, the biological information may include information indicating pulse wave velocity, and the current arousal level may become lower as blood pressure and the pulse wave velocity become lower.

This is because it is known that a person tends to feel drowsy when the pulse wave velocity is low.

The first sensor 30 in this case may include a blood flow sensor.

The first sensor measures changes in blood flow volume in an artery and a vein in each body part of the user using either a laser speckle camera or a camera as the blood flow sensor. The periphery of the user's body is one of such body parts. The first sensor may calculate the pulse wave velocity on the basis of a time difference in a change in blood flow volume between an artery of a measured body part of the user and a vein in the periphery.

Alternatively, for example, the biological information may include information indicating blood pressure, and the current arousal level may become lower as the blood pressure becomes lower.

This is because it is known that a person tends to feel drowsy when the blood pressure is low.

The first sensor 30 in this case may include a blood pressure sensor.

The first sensor 30 may detect the blood pressure of the user using the blood pressure sensor.

Alternatively, for example, the biological information may include information indicating the pulse wave velocity and the blood pressure.

When Biological Information Includes Information Indicating Blink Speed and Movement of Eyes Alternatively, for example, the biological information may include information indicating the blink speed of the user and the movement of the user's eyes, and the current arousal level may become lower as a current blink speed of the user becomes lower or a current movement of the user's eyes become fewer. This is because it is known that a person tends to feel drowsy when the blink speed of the person is low or the movement of the person's eyes is few.

The first sensor 30 in this case may detect the current blink speed of the user or the current movement of the user's eyes by capturing an image of the user's eyes using a camera.

Environment Information Obtaining Unit 12

The environment information obtaining unit 12 obtains current environment information detected by the second sensor 40.

In the present embodiment, the environment information obtaining unit 12 communicates with the second sensor 40 directly or through the communication unit 15 to obtain the current environment information. The environment information may be information indicating illumination, ambient temperature, $CO_2$ concentration, wind speed, vibration, or any combination of these pieces of information. The second sensor may be an illumination sensor, an ambient temperature sensor, a $CO_2$ concentration sensor, a wind speed sensor, or a vibration sensor, or may detect environment information using any combination of these sensors.

If the environment information includes $CO_2$ concentration, for example, the second sensor 40 may measure the $CO_2$ concentration using a $CO_2$ concentration sensor, or may include an infrared light source and a light receiving unit and measure $CO_2$ concentration using $CO_2$ concentration distribution measuring means that measures $CO_2$ concentration in a certain direction through absorption spectroscopy.

Alternatively, the environment information may include the amount of solar radiation. In this case, the second sensor 40 may measure the amount of solar radiation using solar radiation measuring means or a thermal image sensor, and the environment information obtaining unit 12 may obtain a current amount of solar radiation measured by the second sensor 40.

If there are a plurality of second sensors 40, the environment information obtaining unit 12 may obtain environment information from a second sensor 40 selected in accordance with a type, a model, or an installed position of a second sensor 40 specified by the user in advance.

Processing Unit 13

Figure 2:
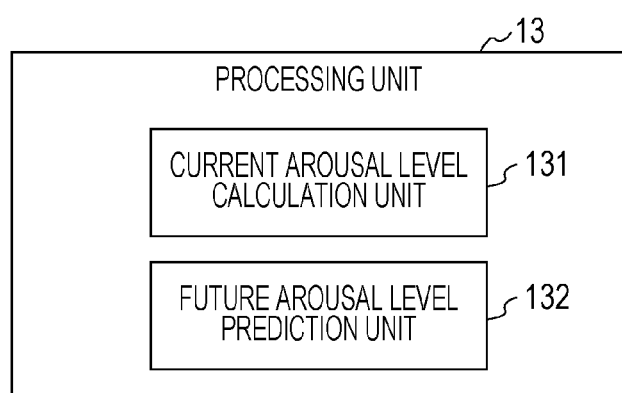
FIG. 2 is a block diagram illustrating a detailed configuration of a processing unit illustrated in FIG. 1.
Figure 3:
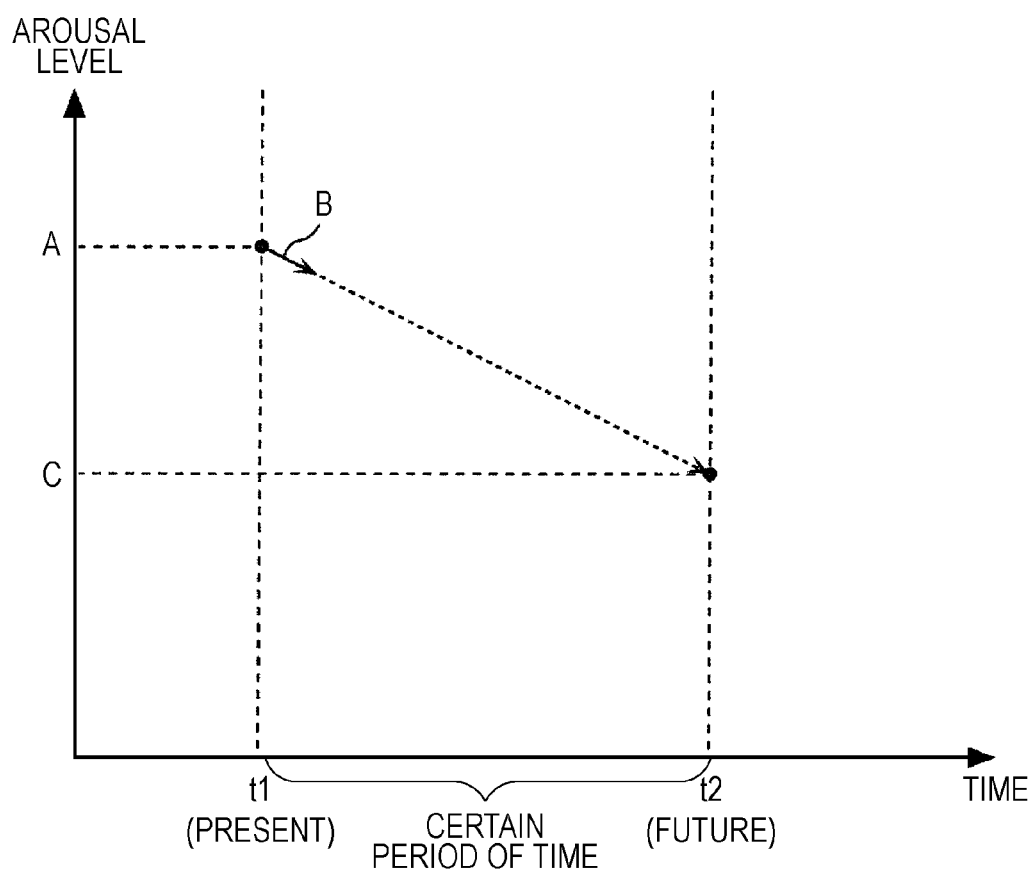
FIG. 3 is a diagram illustrating a method for predicting a future arousal level according to the first embodiment.

FIG. 2 is a block diagram illustrating a detailed configuration of the processing unit 13 illustrated in FIG. 1. FIG. 3 is a diagram illustrating a method for predicting a future arousal level according to the first embodiment.

The processing unit 13 predicts a future arousal level, which is an arousal level a certain period of time later, on the basis of the current biological information regarding the user obtained by the biological information obtaining unit 11 and the current environment information obtained by the environment information obtaining unit 12. The certain period of time refers to a few minutes to tens of minutes, namely, for example, two, three, or 10 minutes. If the arousal level prediction apparatus 10 is mounted on an automobile, the certain period of time is included in a time taken to arrive at a destination input by the user to a navigation system installed in the automobile.

In the present embodiment, as illustrated in FIG. 2, the processing unit 13 includes a current arousal level calculation unit 131 and a future arousal level prediction unit 132.

The current arousal level calculation unit 131 calculates the current arousal level of the user on the basis of the current biological information regarding the user obtained by the biological information obtaining unit 11.

The future arousal level prediction unit 132 predicts the future arousal level, which is the arousal level the certain period of time later, on the basis of the current arousal level calculated by the current arousal level calculation unit 131 and the current environment information obtained by the environment information obtaining unit 12. More specifically, the future arousal level prediction unit 132 predicts the future arousal level by estimating a rate of decrease in the arousal level on the basis of how likely it is for a person to become drowsy in an environment indicated by the current environment information and correcting the current arousal level to the arousal level the certain period of time later using the estimated rate of decrease.

More specifically, as illustrated in FIG. 3, the future arousal level prediction unit 132 estimates a rate of decrease in the arousal level indicated by an arrow B, for example, on the basis of how likely it is for a person to become drowsy in an environment around the user indicated by environment information at a present time t1. The future arousal level prediction unit 132 then calculates a future arousal level at a time t2 a certain period of time later using the estimated rate of decrease (arrow B) and a current arousal level A at the present time t1. The future arousal level prediction unit 132 can thus predict a future arousal level by correcting a current arousal level to an arousal level a certain period of time later using an estimated rate of decrease.

If the environment information includes information indicating illumination and the second sensor 40 is an illumination sensor, for example, the current environment information may be information indicating a current illumination around the user. In this case, the rate of decrease in the arousal level estimated by the future arousal level prediction unit 132 becomes higher as the current illumination indicated by the current environment information becomes lower. This is because it is known that a person is unlikely to become drowsy in a bright environment.

If the environment information includes information indicating wind speed and the second sensor 40 is a wind speed sensor, for example, the current environment information may be information indicating a current wind speed around the user. In this case, the rate of decrease in the arousal level estimated by the future arousal level prediction unit 132 becomes higher as the current wind speed indicated by the current environment information becomes lower. This is because it is known that a person is unlikely to become drowsy when wind is strong.

If the environment information includes information indicating $CO_2$ concentration and the second sensor 40 is a $CO_2$ concentration sensor, for example, the current environment information may be information indicating a current $CO_2$ concentration around the user. In this case, the rate of decrease in the arousal level estimated by the future arousal level prediction unit 132 becomes higher as the current $CO_2$ concentration indicated by the current environment information becomes higher. This is because it is known that a person is unlikely to become drowsy when $CO_2$ concentration around the person is low.

If the environment information includes information indicating vibration and the second sensor 40 is a vibration sensor, for example, the current environment information may be information indicating a current vibration around the user. In this case, the rate of decrease in the arousal level estimated by the future arousal level prediction unit 132 becomes higher as the current vibration indicated by the current environment information becomes larger. This is because it is known that a person is unlikely to become drowsy when vibration applied to the person is small and that a person is likely to become drowsy when the frequency of vibration applied to the person is lower than that of heartbeat within a range of 10% or when the frequency of vibration applied to the person is lower than that of respiration within a range of 10%.

If the environment information includes information indicating ambient temperature and the second sensor 40 is an ambient temperature sensor, for example, the current environment information may be information indicating a current ambient temperature around the user (e.g., a temperature of a room where the user is currently located). In this case, the rate of decrease in the arousal level estimated by the future arousal level prediction unit 132 becomes higher as the current ambient temperature indicated by the current environment information becomes higher. This is because it is known that a person is unlikely to become drowsy when ambient temperature is low. Because comfortable temperature is different between winter and summer, namely 20° C. in winter and 25° C. in summer, whether ambient temperature is high or low may be evaluated on the basis of the comfortable temperature corresponding to the season.

If the environment information includes information indicating ambient temperature distribution and the second sensor 40 is a radiation temperature sensor, for example, the current environment information may indicate a current ambient temperature distribution around the user (e.g., a temperature distribution in a room where the user is currently located). Because it is known that a person is unlikely to become drowsy when temperatures around the head, the hands, and the feet are low and temperatures around the chest and the abdomen are high, the rate of decrease in the arousal level estimated by the future arousal level prediction unit 132 becomes lower as a value obtained by subtracting a temperature around the hands or the feet from a temperature around the chest or the abdomen becomes larger.

A relationship illustrated in FIG. 3 may be obtained, for example, as a result of experiments for obtaining relationships between the duration of driving and the arousal level in various environments.

If the second sensor 40 detects illumination, for example, the experiments for obtaining the relationships between the duration of driving and the arousal level are conducted while a subject is driving under a condition of a constant illumination.

At this time, the experiments for obtaining the relationships between the duration of driving and the arousal level are conducted with various values of the constant illumination.

The same holds when the second sensor 40 detects information other than illumination, namely, for example, ambient temperature, $CO_2$ concentration, wind speed, or vibration.

In doing so, the relationships between the duration of driving and the arousal level can be obtained in various environments.

The subject may or may not be the user. The number of subjects may be one or more. If there are a plurality of subjects, the relationships between the duration of driving and the arousal level may be results obtained by performing a statistical process, such as averaging, on relationships between the duration of driving and the arousal level obtained from the subjects.

The above-described relationships may be associated with environments in which experiments have been conducted, for example, and stored in a memory (not illustrated) of the arousal level prediction apparatus 10 in advance.

The processing unit 13 may read, from the memory, a relationship between the duration of driving and the arousal level corresponding to an environment indicated by the current environment information obtained by the environment information obtaining unit 12 and predict a future arousal level or estimate a rate of decrease in the arousal level using the relationship read from the memory.

Control Unit 14

The control unit 14 (i) issues a notification to the user or (ii) controls another device 20 on the basis of the future arousal level. The control unit 14 performs the notification or the control only if the future arousal level is lower than a certain threshold. The certain threshold is an arousal level low enough to hinder the user's current activity. In order to increase such an arousal level, certain measures need to be taken. The other device 20 is a device to be controlled, and may be an air conditioner or a lighting device, for example, installed in the same space in which the arousal level prediction apparatus 10 is installed or a personal computer (PC) including a display unit used by the user. The other device 20 may be a chair or a steering wheel of an automobile in contact with the user.

In the present embodiment, the control unit 14 determines whether a predicted future arousal level is lower than the certain threshold. If the predicted future arousal level is lower than the certain threshold, the control unit 14 may output a notification signal to a mobile terminal owned by the user through the display unit 16 or the communication unit 15 to display a screen for notifying the user that the future arousal level is lower than the certain threshold. In this case, the user can try to increase his/her arousal level by drinking a cup of coffee or opening a window of the automobile.

If the predicted future arousal level is lower than the certain threshold, the control unit 14 may output a control signal to the other device 20 through the communication unit 15 to control the other device 20 in such a way as to increase the arousal level of the user. If the other device 20 is an air conditioner installed in the same space in which the arousal level prediction apparatus 10 is installed, for example, the control unit 14 may change a setting temperature or an air volume of the air conditioner when the future arousal level is lower than the certain threshold. By blowing cooling air early in this manner, for example, it becomes possible to suppress a decrease in the current arousal level. A decrease in the arousal level can be further reduced by cooling the periphery of the user's body, namely the face, the hands, or the feet. It is known that a person tends to feel that ambient temperature has dropped by 2° C., for example, when the user's head is exposed to a wind of 0.5 m/s.

If the environment information includes information indicating $CO_2$ concentration and the other device 20 is a $CO_2$ concentration reducing apparatus, such as a ventilation fan, installed in the same space in which the arousal level prediction apparatus 10 is installed, for example, the control unit 14 may activate the $CO_2$ concentration reducing apparatus such as a ventilation fan when a future arousal level is lower than the certain threshold. By reducing the $CO_2$ concentration early in this manner, for example, it becomes possible to suppress a decrease in the current arousal level. If the environment information includes information indicating $CO_2$ concentration and the other device 20 is an oxygen enrichment membrane installed in the same space in which the arousal level prediction apparatus 10 is installed, for example, the control unit 14 may control the oxygen enrichment membrane in such a way as to increase $O_2$ concentration or $N_2$ concentration when a future arousal level is lower than the certain threshold.

If the other device 20 is a lighting device installed in the same space in which the arousal level prediction apparatus 10 is installed, for example, the control unit 14 may increase the brightness of the lighting device when a future arousal level is lower than the certain threshold. By increasing the brightness early in this manner, it becomes possible to suppress a decrease in the current arousal level. A decrease in the arousal level can be further reduced by adjusting the direction of the lighting device in order to increase the amount of light that reaches the user's eyes.

If the other device 20 is a PC including a display unit used by the user, for example, the control unit 14 may change a color or luminance of the display unit of the PC when a future arousal level is lower than the certain threshold. The PC may be a head-up display (HUD) or a mobile terminal or an information terminal including a touch panel as a display unit.

If the other device 20 is a chair or a steering wheel of an automobile in contact with the user, for example, the control unit 14 may generate vibration by activating a driving unit included in the chair or the steering wheel when a future arousal level is lower than the certain threshold. Here, if the future arousal level is lower than the certain threshold but the current arousal level is higher than the certain threshold, the control unit 14 may activate the driving unit in a first driving mode, and if both the future arousal level and the current arousal level are lower than the certain threshold, the control unit 14 may activate the driving unit in a second driving mode, in which vibration is stronger than in the first driving mode.

If the other device 20 is a music player such as an audio component or a radio cassette player, for example, the control unit 14 may activate the music player to play music when a future arousal level is lower than the certain threshold.

If there are a plurality of other devices 20, the control unit 14 may select and control one of the other devices 20 in accordance with one of rules (priority modes) specified by the user in advance. The priority modes include, for example, a power-saving priority mode, an arousal induction priority mode, an ambient temperature comfortability priority mode, a relaxing mode, and a multiple priority mode. A case will be described hereinafter as an example in which there are a plurality of other devices 20, namely a lighting device, an air conditioner, and a music player, installed in the same space in which the arousal level prediction apparatus 10 is installed.

If the user selects the power-saving priority mode, the control unit 14 may select and control the lighting device or the music player as another device 20, not the air conditioner, whose power consumption is high. If the user selects the arousal induction priority mode, the control unit 14 may select and control the air conditioner, which increases the arousal level of the user most effectively.

If the user selects the ambient temperature comfortability priority mode, the control unit 14 may select and control the air conditioner in such a way as to blow air only to the user's hands, feet, and head so that the user's comfort is not affected. If the user selects the relaxing mode, the control unit 14 may cause the lighting device to light up in a warm color so that the user's mental fatigue can be reduced.

If the selects the multiple priority mode, the control unit 14 may control all the other devices 20 including the lighting device, the air conditioner, and the music player.

Communication Unit 15

The communication unit 15 includes a processor and a communication interface and has a function of communication with another device 20, which is a device to be controlled, or the like. In the present embodiment, the communication unit 15 transmits, to the other device 20, a control signal that enables the control unit 14 to control the other device 20. The communication unit 15 also communicates with the first sensor 30, obtains the current biological information from the first sensor 30, and transmits the current biological information to the biological information obtaining unit 11. The communication unit 15 also communicates with the second sensor 40, obtains the current environment information from the second sensor 40, and transmits the current environment information to the environment information obtaining unit 12. The communication unit 15 may also communicate with a device operated by the user or the like and receive information indicating a priority mode selected by the user.

Display Unit 16

The display unit 16 is an organic electroluminescence device, a liquid crystal display, a plasma display panel (PDP), or the like and displays a control mode of the control unit 14, a calculated current arousal level, a predicted future arousal level, and the like. The display unit 16 may include a touch panel display, which is used for inputting information indicating a priority mode selected by the user and displaying the priority mode.

Figure 4:
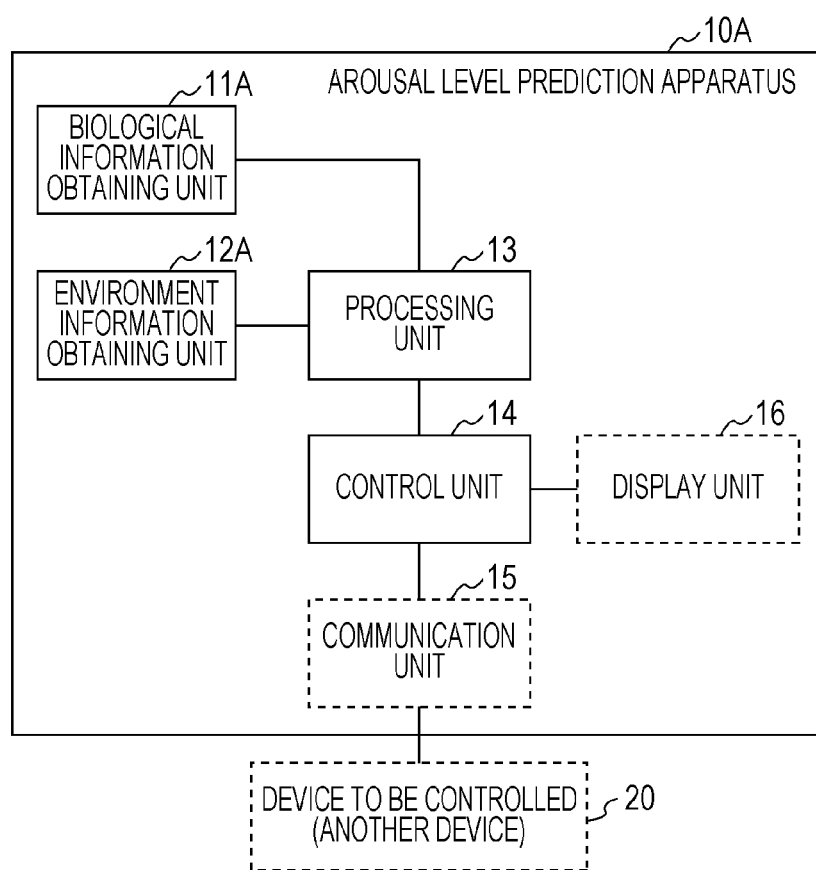
FIG. 4 is a block diagram illustrating another example of the configuration of the arousal level prediction apparatus according to the first embodiment.

Although the biological information obtaining unit 11 obtains biological information from the first sensor 30, which is separate from the biological information obtaining unit 11, and the environment information obtaining unit 12 obtains environment information from the second sensor 40, which is separate from the environment information obtaining unit 12, in the above-described arousal level prediction apparatus 10, the configuration of the arousal level prediction apparatus 10 is not limited to this. As illustrated in FIG. 4, an arousal level prediction apparatus 10A may include a biological information obtaining unit 11A into which the first sensor 30 is incorporated and an environment information obtaining unit 12A into which the second sensor 40 is incorporated. That is, the biological information obtaining unit 11A may obtain current biological information regarding the user using a sensor that obtains biological information, and the environment information obtaining unit 12A may obtain current environment information using a sensor that obtains environment information indicating an environment around the user. FIG. 4 is a block diagram illustrating the configuration of the arousal level prediction apparatus 10A according to the first embodiment. The same components illustrated in FIG. 1 are given the same reference numerals, and detailed description thereof is omitted.

Operation of Arousal Level Prediction Apparatus 10

Figure 5:
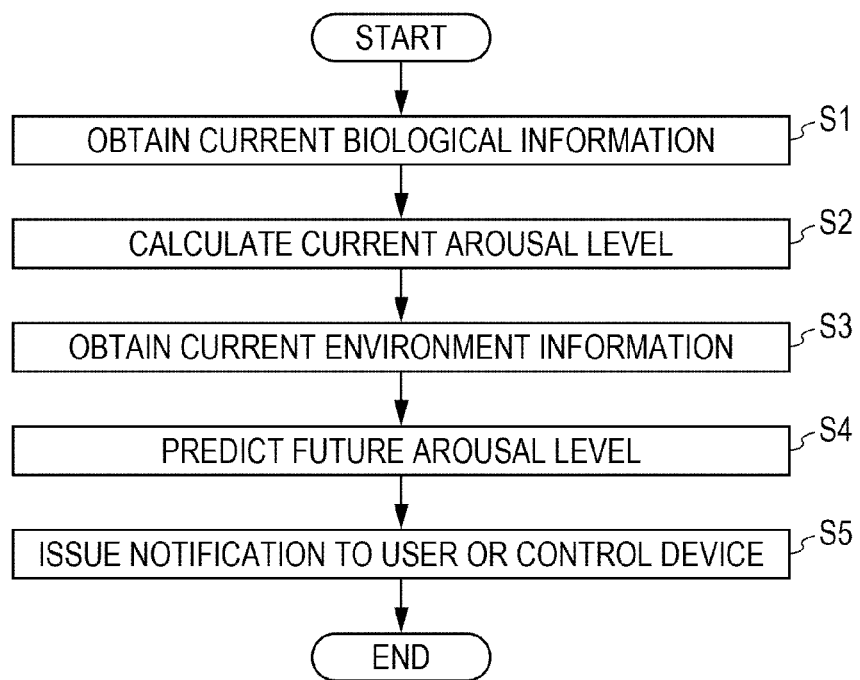
FIG. 5 is a flowchart illustrating an overall operation of the arousal level prediction apparatus illustrated in FIG. 1.
Figure 6:
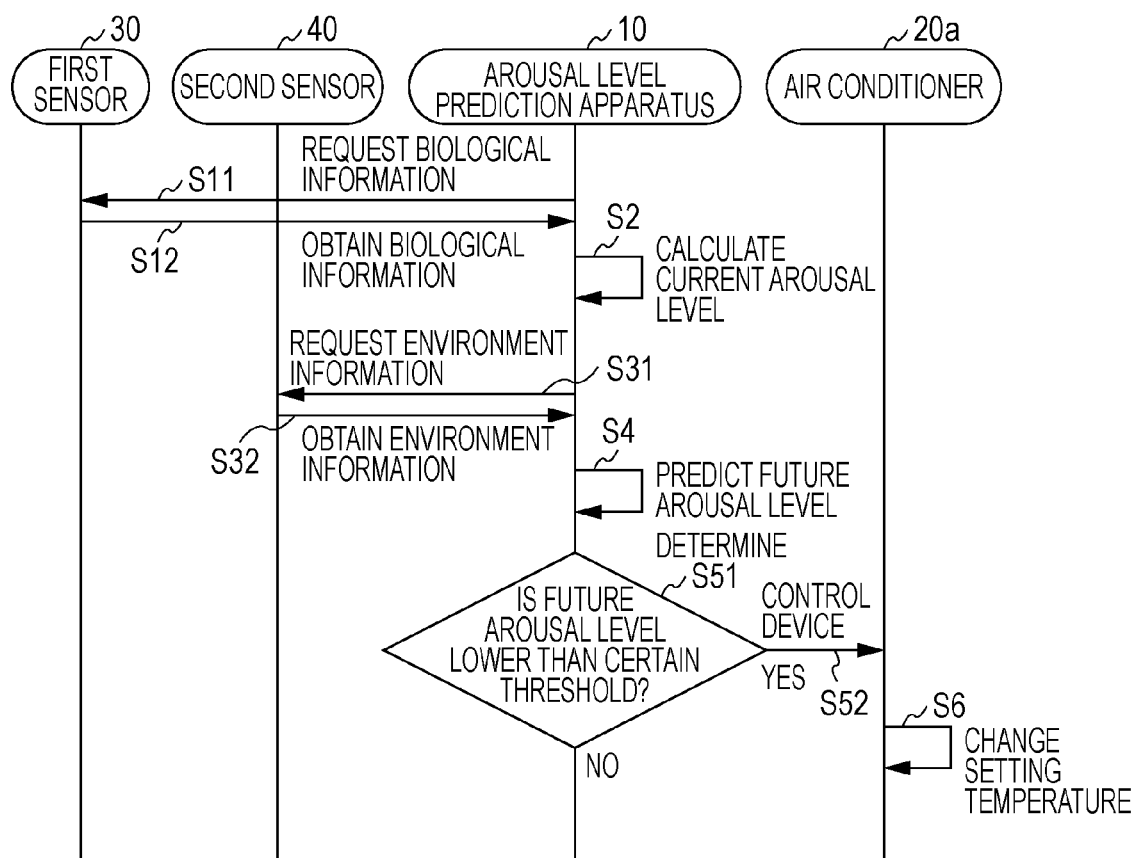
FIG. 6 is a sequence diagram illustrating a procedure of the operation of the arousal level prediction apparatus illustrated in FIG. 1.

Next, the operation of the arousal level prediction apparatus 10 will be described with reference to FIGS. 5 and 6. FIG. 5 is a flowchart illustrating an overall operation of the arousal level prediction apparatus 10 illustrated in FIG. 1. FIG. 6 is a sequence diagram illustrating a procedure of the operation of the arousal level prediction apparatus 10 illustrated in FIG. 1. In the following description, the other device 20 is an air conditioner 20a.

First, the arousal level prediction apparatus 10 obtains the current biological information regarding the user detected by the first sensor 30, which obtains biological information (S1). In the present embodiment, the biological information obtaining unit 11 communicates with the first sensor 30 directly or through the communication unit 15 and requests biological information from the first sensor 30 (S11). The biological information obtaining unit 11 then obtains biological information from the first sensor 30 (S12).

Next, the arousal level prediction apparatus 10 calculates the current arousal level of the user on the basis of the obtained current biological information (S2).

Next, the arousal level prediction apparatus 10 obtains the current environment information detected by the second sensor 40 that obtains environment information indicating an environment around the user (S3). In the present embodiment, the environment information obtaining unit 12 communicates with the second sensor 40 directly or through the communication unit 15 and requests environment information from the second sensor 40 (S31). The environment information obtaining unit 12 then obtains environment information from the second sensor 40 (S32). The processing in steps S2 and S3 need not be performed in this order, but the processing in step S3 may be performed first.

Next, the arousal level prediction apparatus 10 predicts the future arousal level, which is the arousal level the certain period of time later, on the basis of the obtained current arousal level and the obtained current environment information (S4).

Next, the arousal level prediction apparatus 10 issues a notification to the user or controls the other device 20 on the basis of the predicted future arousal level (S5). In the present embodiment, first, the control unit 14 determines whether the predicted future arousal level is lower than the certain threshold (S51). Next, if the predicted future arousal level is lower than the certain threshold (Y in S51), the control unit 14 transmits a control signal for changing, say, a setting temperature of the air conditioner 20a to the air conditioner 20a through the communication unit 15 (S52).

The air conditioner 20a then changes the setting temperature thereof in accordance with the received control signal (S6).

If the calculated current arousal level is significantly higher than the certain threshold, the arousal level prediction apparatus 10 may end the operation without performing the processing in step S3 and later. This is because when it is apparent that the future arousal level will not become lower than the certain threshold, the processing need not be performed.

Advantageous Effects

As described above, according to the present embodiment, the future arousal level can be predicted, and a method for predicting an arousal level and an arousal level prediction apparatus capable of detecting a decrease in the arousal level of the user earlier can be achieved. As a result, the user can be notified of necessary information displayed at an appropriate position at an appropriate timing.

How likely it is for the user to become drowsy in an environment around the user can be calculated using only environment information, and, for example, whether an office is suitable for work can be evaluated. When biological information is used, however, individual differences between users and a physical condition of the user of the day can be taken into consideration, and the future arousal level can be predicted more accurately using both the environment information and the biological information.

In the method for predicting an arousal level and the arousal level prediction apparatus in the present embodiment, therefore, the future arousal level is calculated using the current environment information and the current arousal level calculated from the current biological information.

As a result, an unnoticed sign of a decrease in the arousal level of the user can be detected earlier than in a system in the examples of the related art. The arousal level can be increased without a strong stimulus, and a decrease in the arousal level of the user can be suppressed with a mild stimulus, which is advantageous. That is, since the user can be notified on the basis of the future arousal level that the arousal level of the user might decrease or another device can be controlled in such a way as to provide a mild stimulus for maintaining the arousal level, a decrease in the arousal level of the user can be suppressed.

If the arousal level prediction apparatus 10 is installed in an office, for example, a future arousal level of each user in the office, that is, each worker, is predicted, and ambient temperature around each user, the luminance of a lighting device near each worker, or the like is adjusted in order to create an environment in which each worker is unlikely to become drowsy. If the arousal level prediction apparatus 10 is mounted on an automobile, for example, a future arousal level of a user, that is, a driver of the automobile, is predicted, and an environment in which the user is unlikely to become drowsy can be created using a vehicle air conditioner, a ventilation system, a vehicle lighting device, or the like.

A case in which the arousal level prediction apparatus 10 controls an air conditioner as another device 20 will be described hereinafter. If a future arousal level is lower than the certain threshold and it can be predicted that the user is likely to become drowsy, the arousal level prediction apparatus 10 controls the air conditioner in such a way as to decrease ambient temperature. This is because if the air conditioner decreases the ambient temperature in order to suppress a decrease in the arousal level even when the user is unlikely to become drowsy, power is not saved in summer and it is uncomfortable for the user. It is therefore preferable that, as described above, the arousal level prediction apparatus 10 control the air conditioner on the basis of the predicted future arousal level. If the arousal level prediction apparatus 10 controls the air conditioner on the basis of the current arousal level, on the other hand, the ambient temperature decreases after the user becomes drowsy, and it is difficult to suppress a decrease in the arousal level of the user. In the present embodiment, since the future arousal level is predicted and cooling air is blown early, a decrease in the arousal level can be effectively suppressed. A decrease in the arousal level can be effectively suppressed especially by cooling the periphery of the user's body, that is, the user's face, hands, feet, or the like.

Furthermore, the arousal level prediction apparatus 10 may obtain the temperature of the user's body (especially the periphery) as biological information. If the user's body (especially the periphery) is sufficiently cold, the arousal level can be maintained by controlling another device without controlling the air conditioner to blow cooling air even when the future arousal level is lower than the certain threshold and it has been predicted that the user is likely to become drowsy. Alternatively, the arousal level prediction apparatus 10 may obtain the amount of solar radiation on the user as environment information. In this case, because the body temperature of the user increases when the amount of solar radiation on the user is large, the air conditioner is controlled in such a way as to blow stronger cooling air or cooler air to a side of the user's body exposed to sunlight.

Next, a case will be described in which the environment information includes information indicating $CO_2$ concentration and the arousal level prediction apparatus 10 controls a $CO_2$ concentration reducing apparatus, such as a ventilation fan, as another device 20. If the future arousal level is lower than the certain threshold and it can be predicted that the user is likely to become drowsy, the $CO_2$ concentration reducing apparatus is controlled in such a way as to reduce $CO_2$ concentration. This is because power is not saved if $CO_2$ concentration is unnecessarily reduced in order to suppress a decrease in the arousal level even when the user is unlikely to become drowsy. It is therefore preferable that, as described above, the arousal level prediction apparatus 10 control the $CO_2$ concentration reducing apparatus on the basis of the predicted future arousal level.

Similarly, a case will be described in which the environment information includes information indicating $CO_2$ concentration and the arousal level prediction apparatus 10 controls an oxygen enrichment membrane as another device 20. If the future arousal level is lower than the certain threshold and it can be predicted that the user is likely to become drowsy, the arousal level prediction apparatus 10 may control the oxygen enrichment membrane in such a way as to increase $O_2$ concentration or $N_2$ concentration. This is because power is not saved if $O_2$ concentration or $N_2$ concentration is unnecessarily increased in order to suppress a decrease in the arousal level even when the user is unlikely to become drowsy. It is therefore preferable that, as described above, the arousal level prediction apparatus 10 control the oxygen enrichment membrane on the basis of the predicted future arousal level.

A case in which the arousal level prediction apparatus 10 controls a lighting device as another device 20 will be described hereinafter. If the future arousal level is lower than the certain threshold and it can be predicted that the user is likely to become drowsy, the arousal level prediction apparatus 10 may increase the luminance of the lighting device. This is because power is not saved if the luminance is unnecessarily increased in order to suppress a decrease in the arousal level even when the user is unlikely to become drowsy. In summer, in particular, if the lighting device turns on unnecessarily, an air conditioner needs to cool air heated by the lighting device, which is a waste of power. It is therefore preferable that, as described above, the arousal level prediction apparatus 10 control the lighting device on the basis of the predicted future arousal level.

The arousal level prediction apparatus 10 may be incorporated into an information terminal such as a desktop PC, a laptop PC, or a tablet, and a display of the information terminal may include a camera or noncontact sensors (the first sensor 30 and the second sensor 40), such as thermal image sensors or milliwave sensors. In this case, by predicting a future arousal level of the user of the information terminal and increasing the arousal level through adjustment of a color or luminance of the display of the information terminal or intermittent driving, an environment in which the user is unlikely to become drowsy can be created. That is, the arousal level can be maintained by adjusting the color or luminance of the display or performing intermittent driving on the basis of the future arousal level of the user. The method for controlling another device is not limited to this. A small blower near the user's desk or a seat heater mounted on the user's chair may be driven by wirelessly transmitting a result of the prediction, instead. Alternatively, information for controlling each device, not the result of the prediction, based on the result of the prediction may be transmitted.

Second Embodiment

Although the future arousal level is predicted on the basis of the current biological information and the current environment information in the first embodiment, the method for predicting the future arousal level is not limited to this. The future arousal level may be predicted on the basis of these pieces of information and living information regarding the user, such as an activity history. In this case, the accuracy of predicting the future arousal level improves. This case will be described hereinafter as a second embodiment.

Configuration of Arousal Level Prediction Apparatus

Figure 7:
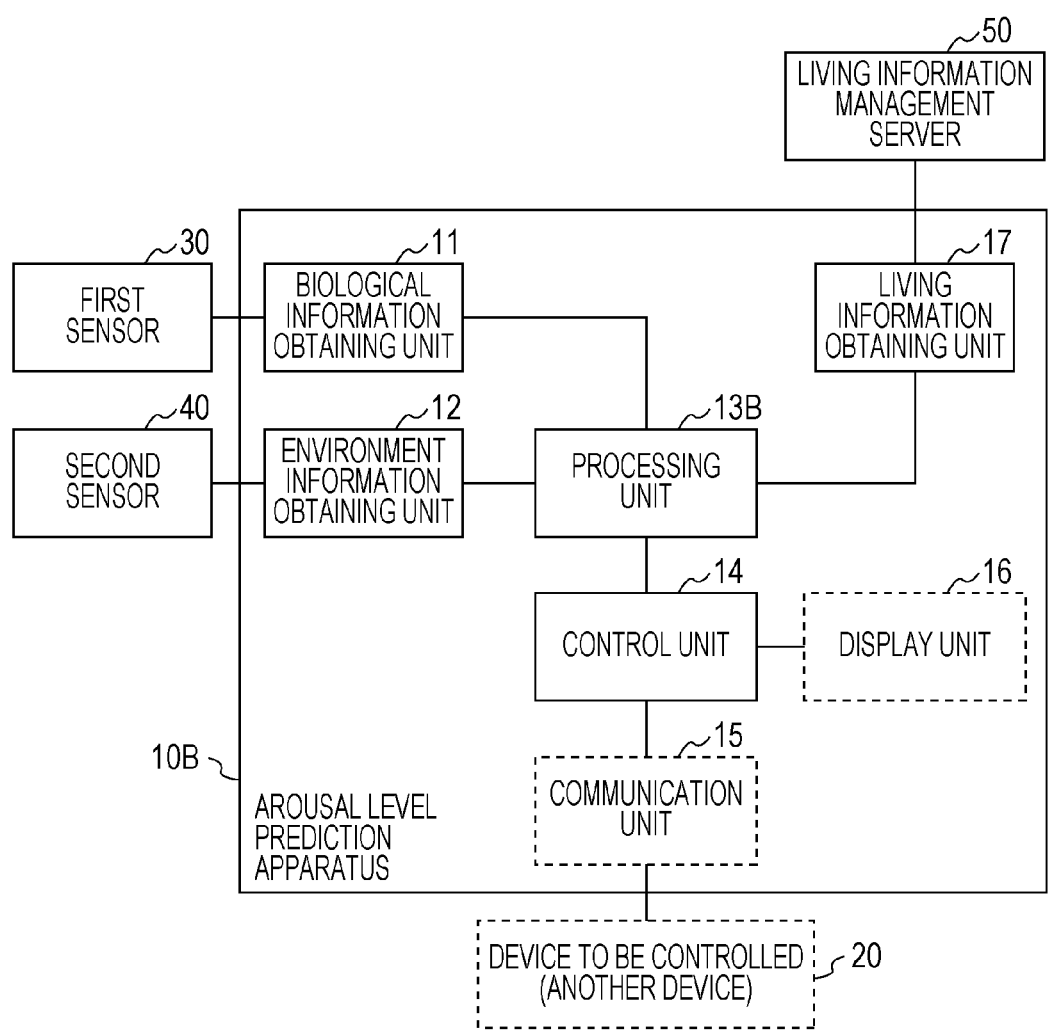
FIG. 7 is a block diagram illustrating the configuration of an arousal level prediction apparatus according to a second embodiment.

FIG. 7 is a block diagram illustrating the configuration of an arousal level prediction apparatus 10B according to the second embodiment. The same components as in FIG. 1 or another figure are given the same reference numerals, and detailed description thereof is omitted.

The arousal level prediction apparatus 10B illustrated in FIG. 7 is different from the arousal level prediction apparatus 10 according to the first embodiment in that a living information obtaining unit 17 is added and the configuration of a processing unit 13B is different from that of the processing unit 13.

Living Information Obtaining Unit 17

The living information obtaining unit 17 obtains information indicating an activity history. In the present embodiment, the living information obtaining unit 17 communicates with a living information management server 50 directly or through the communication unit 15 and obtains living information regarding the user as information indicating an activity history. The living information obtaining unit 17, for example, may obtain sleep information indicating hours of sleep of the user of a previous day, past sleep information indicating hours of sleep of the user in a certain period of time in the past, or information indicating an activity history of the user of the previous day as living information.

When Living Information Indicates Hours of Sleep of Previous Day

The living information, for example, may be sleep information indicating hours of sleep of the user of the previous day. This is because it is known that a person tends to feel drowsy when hours of sleep of the previous day is short. The hours of sleep of the user of the previous day, for example, can be measured by providing a sheet sensor on a bed and measuring a beginning and an end of sleep. Alternatively, a milliwave sensor or an infrared sensor installed in a bedroom may be used as a noncontact sleep meter. In the present embodiment, information measured by the sheet sensor or the sleep meter is transmitted to the living information management server 50 through communication means as living information indicating the hours of sleep of the user of the previous day. The information measured by the sheet sensor or the sleep meter may be directly obtained by the living information obtaining unit 17 as living information indicating the hours of sleep of the user of the previous day.

When Living Information Indicates Past Sleep Information

Alternatively, for example, the living information may be past sleep information indicating hours of sleep of the user in a certain period of time in the past. The past sleep information includes not only sleep information indicating the hours of sleep of the user of the previous day but also information indicating average hours of sleep of the user. This is because necessary hours of sleep varies between individuals and a person whose average hours of sleep is short is unlikely to become drowsy even if the hours of sleep of the previous day is short. In this case, by dividing the hours of sleep of the previous day by the average hours of sleep, how likely it is to become drowsy can be calculated. It can be determined that the user is likely to become drowsy when the hours of sleep of the user of the previous day is shorter than the average hours of sleep of the user by 10% or more.

In the present embodiment, the information measured by the sheet sensor or the sleep meter is transmitted to the living information management server 50 through communication means as living information indicating the hours of sleep of the user of the previous day. The living information management server 50 manages not only the hours of sleep of the user of the previous day but also hours of sleep in the certain period of time in the past. As a result, the living information obtaining unit 17 can obtain not only the hours of sleep of the user of the previous day but also the average hours of sleep from the living information management server 50.

When Living Information Indicates Previous Mealtime

Alternatively, for example, the living information may be information indicating a previous mealtime of the user. This is because it is known that a person tends to become drowsy after a meal. The previous mealtime of the user, for example, may be recorded by the user using a smartphone. The method for obtaining a previous mealtime of the user is not limited to this, but any method may be used insofar as the previous mealtime of the user can be obtained.

When Living Information Indicates Amount of Conversation with Others

Alternatively, for example, the living information may be information indicating the amount of conversation between the user and others. If the amount of speech of the user is small and the amount of speech of others (persons nearby) is large, it can be determined that the user is drowsy, and if the amount of speech of the user is large, it can be determined that the user is not drowsy. Alternatively, the amount of conversation between the user and others may be measured for 10 minutes or more, and if the amount of speech of the user had been large until 10 minutes ago but the current amount of speech of the user is small, it may be determined that the user is drowsy.

When Living Information Indicates Exercise Logs of User

Alternatively, the living information may be information indicating exercise logs of the user. This is because a person tends to become drowsy after performing a certain amount of exercise or more. If a wearable terminal worn by the user, such as a smart watch, and the living information management server 50 are connected to each other, the living information obtaining unit 17 may obtain exercise logs recorded in the wearable terminal from the living information management server 50. The living information obtaining unit 17 may directly obtain the exercise logs recorded in the wearable terminal in cooperation with the wearable terminal, instead.

When Living Information Indicates Another Activity History.

Alternatively, for example, the living information may be information indicated by a scheduler recorded in an information terminal owned by the user or the like. This is because a person tends to become drowsy when there have been a lot of tasks. If the information terminal owned by the user or the like and the living information management server 50 are connected to each other, for example, the living information obtaining unit 17 may obtain the information indicated by the scheduler recorded in the information terminal owned by the user or the like from the living information management server 50. The living information obtaining unit 17 may directly obtain the information indicated by the scheduler recorded in the information terminal or the like in cooperation with the information terminal or the like.

When Living Information Indicates Acceleration History or Driving History of the Vehicle If the arousal level prediction apparatus 10B is mounted on a vehicle such as an automobile, the living information may be information indicating an acceleration history or a driving history of the vehicle. This is because the processing unit 13B, which will be described later, can use this kind of information to accurately calculate the future arousal level of the user. It is known that, for example, a person tends to become drowsy when driving on a relatively straight road and is unlikely to become drowsy when driving on a winding road.

Processing Unit 13B

The processing unit 13B predicts a future arousal level, which is an arousal level a certain period of time later, on the basis of the current biological information obtained by the biological information obtaining unit 11, the current environment information obtained by the environment information obtaining unit 12, and the biological information obtained by the living information obtaining unit 17.

More specifically, if the living information is information indicating exercise logs of the user and the exercise logs indicate that the user has performed the certain amount of exercise or more, for example, the processing unit 13B may decrease the future arousal level predicted on the basis of the current arousal level and the current environment information.

If the living information is information indicated by the scheduler recorded in the information terminal owned by the user or the like and the scheduler indicates that there have been a lot of tasks, for example, the processing unit 13B may decrease the future arousal level predicted on the basis of the current arousal level and the current environment information.

If the living information is information indicating an acceleration history or a driving history of a vehicle, for example, the processing unit 13B may correct the future arousal level predicted on the basis of the current arousal level and the current environment information using an arousal level decrease progress speed estimated on the basis of the acceleration history or the driving history.

Operation of Arousal Level Prediction Apparatus

Figure 8:
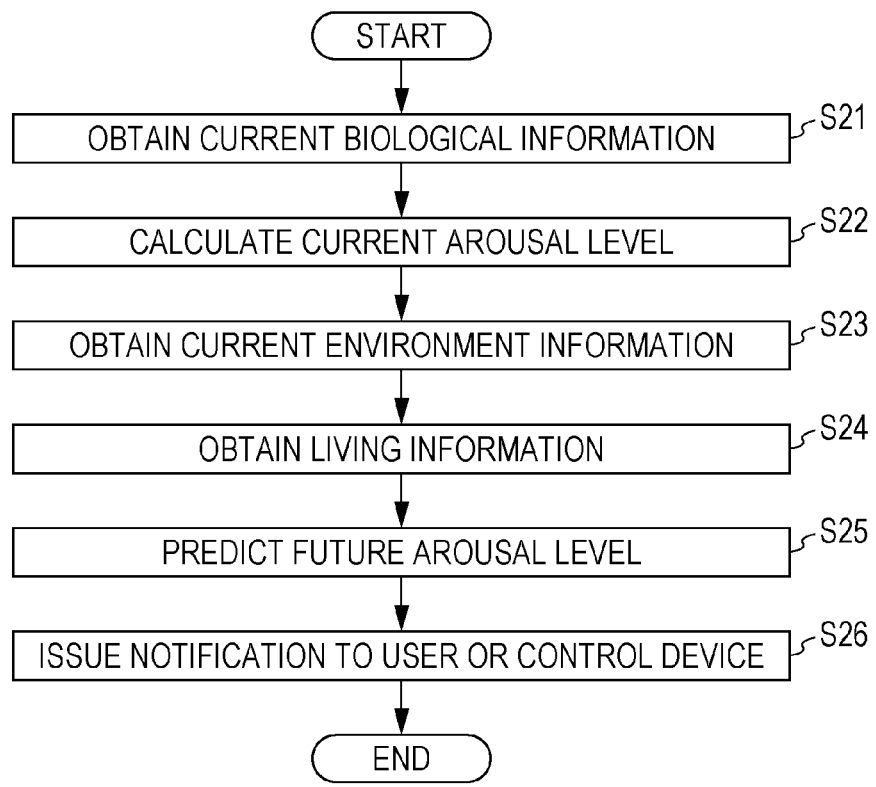
FIG. 8 is a flowchart illustrating an overall operation of the arousal level prediction apparatus illustrated in FIG. 7.

Next, the operation of the arousal level prediction apparatus 10B will be described with reference to FIG. 8. FIG. 8 is a flowchart illustrating an overall operation of the arousal level prediction apparatus 10B illustrated in FIG. 7. Processing in steps S21 to S23 and S26 illustrated in FIG. 8 is the same as steps S1 to S3 and S5, respectively, illustrated in FIG. 5, and detailed description thereof is omitted. Processing in steps S24 and S25, which are different from the steps according to the first embodiment, will be described hereinafter.

In step S24, the arousal level prediction apparatus 10B obtains the living information regarding the user from the living information management server 50 or the like. In the present embodiment, the living information obtaining unit 17 communicates with the living information management server 50 directly or through the communication unit 15 and obtains the living information such as the sleep information indicating the hours of sleep of the user of the previous day, the past sleep information indicating the hours of sleep of the user in the certain period of time in the past, or the activity history of the user of the previous day.

Next, in step S25, the arousal level prediction apparatus 10B predicts the future arousal level, which is the arousal level the certain period of time later, on the basis of the current biological information regarding the user obtained by the biological information obtaining unit 11, the current environment information obtained by the environment information obtaining unit 12, and the biological information obtained by the living information obtaining unit 17.

Advantageous Effects

As described above, according to the present embodiment, since the future arousal level can be predicted, a method for predicting an arousal level and an arousal level prediction apparatus capable of detecting a decrease in the arousal level of the user earlier can be achieved. As a result, the user can be notified of necessary information displayed at an appropriate position at an appropriate timing.

More specifically, the method for predicting an arousal level and the arousal level prediction apparatus according to the present embodiment can predict the future arousal level more accurately using the living information such as the activity history of the user as well as the current environment information and the current arousal level calculated from the current biological information.

Although the method for predicting an arousal level and the arousal level prediction apparatus predict the future arousal level in the first and second embodiments, what is predicted is not limited to this. A degree of drowsiness, fatigue, tension, or anxiousness of the user in the future may be predicted, instead.

An example of a case in which the drowsiness of the user is predicted will be described hereinafter.

Because the heart rate, a ratio of an LF component to an HF component of the heart rate, that is, LF/HF, and the blood pressure begin to decrease when the user begins to become drowsy, these pieces of information are suitable to detect initial drowsiness (predict drowsiness). Rates at which these pieces of information change in accordance with the progress of drowsiness, however, vary between individuals (users). By learning values of the heart rate, the LF/HF, and the blood pressure at a time when each user is widely awake and at a time when each user is significantly drowsy (about drowsiness level 4), therefore, the accuracy of predicting drowsiness improves. If the arousal level prediction apparatus in the present embodiment is mounted on an automobile, for example, the user (driver) is determined to be widely awake about five minutes after the user gets in the automobile, and a state of the user while the user is driving in a wiggly line is determined as drowsiness level 4. Values of the heart rate, the LF/HF, and the blood pressure at these points in time are then stored. As a result, the accuracy of predicting drowsiness improves.

In this example, it is assumed that five drowsiness levels, namely drowsiness levels 1 to 5, are defined. The state of the user defined by drowsiness levels 1 to 5, for example, is determined by the processing unit 13 using the information obtained from the biological information obtaining unit 11, the environment information obtaining unit 12, or the living information obtaining unit 17 or information obtained from a sensor mounted on the automobile (e.g., a sensor that detects a steering angle), a navigation system, or the like.

Drowsiness level 1, for example, may be a state in which the user is widely awake.

Drowsiness level 2, for example, is a drowsiness level at which the arousal level of the user is lower (more drowsy) than in drowsiness level 1. Drowsiness level 2, for example, is a drowsiness level at which the arousal level of the user is higher (less drowsy) than at drowsiness level 3.

Drowsiness level 3, for example, is a drowsiness level at which the arousal level of the user is lower than at drowsiness level 2 but higher than at drowsiness level 4.

Drowsiness level 5, for example, is a drowsiness level at which the arousal level of the user is lower than at drowsiness level 4.

Drowsiness level 5, for example, may be a state in which the user is asleep or the user can be regarded as being asleep.

The processing unit 13 determines that the drowsiness level is 4, for example, if the processing unit 13 receives, from a navigation system, which is not illustrated, information indicating that the driver is currently driving on a straight road and receives information indicating that a frequency at which an angle detected by a sensor that detects a steering angle exceeds a certain threshold is higher than a certain frequency.

If determining that the drowsiness level of the user is 4, the processing unit 13 obtains the biological information regarding the user using the biological information obtaining unit 11 as the current arousal level of the user and stores the obtained biological information in the memory (not illustrated) of the arousal level prediction apparatus 10. As a result, the biological information regarding the user corresponding to drowsiness level 4 can be obtained. The arousal level of the user corresponding to drowsiness level 4 is then calculated using this biological information.

The same holds for drowsiness levels 1, 2, 3, and 5. If determining that the state of the user corresponds to each drowsiness level, the processing unit 13 obtains the biological information regarding the user corresponding to each drowsiness level from the biological information obtaining unit 11 and stores the obtained biological information in the memory (not illustrated) of the arousal level prediction apparatus 10. The processing unit 13 then calculates the arousal level corresponding to each drowsiness level from the biological information.

As a result, drowsiness levels 1 to 5 and the corresponding arousal levels can be associated with each other.

The biological information regarding the user obtained by the biological information obtaining unit 11 at this time is the number of blinks, the blink speed, the heart rate, or the blood pressure of the user or the like (multimodal).

With respect to drowsiness levels 2 to 5, it is desirable to store, in the memory, the biological information regarding the user corresponding to each drowsiness level and information regarding a time taken for a previous corresponding drowsiness level to change to each drowsiness level.

In doing so, for example, in an environment indicated by the environment information obtained by the environment information obtaining unit 12, points corresponding to drowsiness levels 1 to 5 can be plotted in a graph in which a horizontal axis represents time since a beginning of driving and a vertical axis represents the arousal level as illustrated in FIG. 3. These points may be substantially aligned with one another like the straight line illustrated in FIG. 3, for example, through regression calculation.

The biological information (measured values) regarding the user corresponding to the arousal levels corresponding to drowsiness levels 1 to 5, for example, may be obtained through the experiments for obtaining the relationships between the duration of driving and the arousal level conducted on the user in various environments and stored in the memory (not illustrated) at the arousal level prediction apparatus 10 in advance.

If the arousal level of the user is drowsiness level 4, for example, it can be reliably predicted that the arousal level of the user will change to drowsiness level 5 in course of time. In order to arouse the user whose drowsiness level is 4, however, a strong stimulus is necessary. If such a stimulus is given, the user might be surprised during driving, which might affect the driving operation.

If the certain threshold is set at the arousal level of the user corresponding to drowsiness level 4 and the control unit 14 gives a stimulus to the user using another device 20 after the processing unit 13 determines that the current drowsiness level of the user is 4, for example, the stimulus to be given to the user might be too strong, which might affect the driving operation.

In the present embodiment, for example, the processing unit 13 predicts, before the drowsiness of the user actually reaches drowsiness level 4, that the drowsiness level of the user is likely to change to drowsiness level 4 in a certain period of time. The control unit 14 then gives a stimulus to the user using another device 20.

The stimulus to be given to the user to arouse the user whose drowsiness level is 3 is milder than the stimulus to be given to the user to arouse the user whose drowsiness level is 4. That is, if the drowsiness level of the user is 3, a strong stimulus need not be given to the user to arouse the user, compared to when the drowsiness level of the user is 4.

In addition, the stimulus to be given to the user to arouse the user whose drowsiness level is 2 is milder than the stimulus to be given to the user to arouse the user whose drowsiness level is 3. That is, if the drowsiness level of the user is 2, a strong stimulus need not be given to the user to arouse the user, compared to when the drowsiness level of the user is 3.

That is, when the drowsiness level of the user is low (the arousal level is high), the stimulus to be given to the user to arouse the user is mild.

That is, as the current drowsiness level of the user becomes lower, the stimulus to be given to the user by the control unit 14 by controlling the other device 20 (an air conditioner or a lighting device) to arouse the user (drowsiness level 1) becomes milder.

When the arousal level of the user is high, for example, the user can, during driving, take a look at a screen of a mobile terminal on which a notification has been issued. If, when the drowsiness level of the user is lower than 4, the processing unit 13 predicts that the drowsiness level of the user will change to drowsiness level 4 in a certain period of time and the control unit 14 notifies the mobile terminal of the prediction, the user can arouse himself.

Although an example in which the certain threshold is set at the arousal level of the user corresponding to drowsiness level 4 has been described, the certain threshold is not limited to this. The certain threshold may be associated with an arousal level at which the current driving operation of the user is affected.

If the relationships between time (the duration of driving) and the arousal level of the user are stored in the memory (not illustrated) of the arousal level prediction apparatus 10 in advance, for example, the arousal level prediction apparatus 10 (e.g., the processing unit 13) may correct a relationship using the biological information used for calculating the arousal level corresponding to drowsiness level 4.

Figure 9:
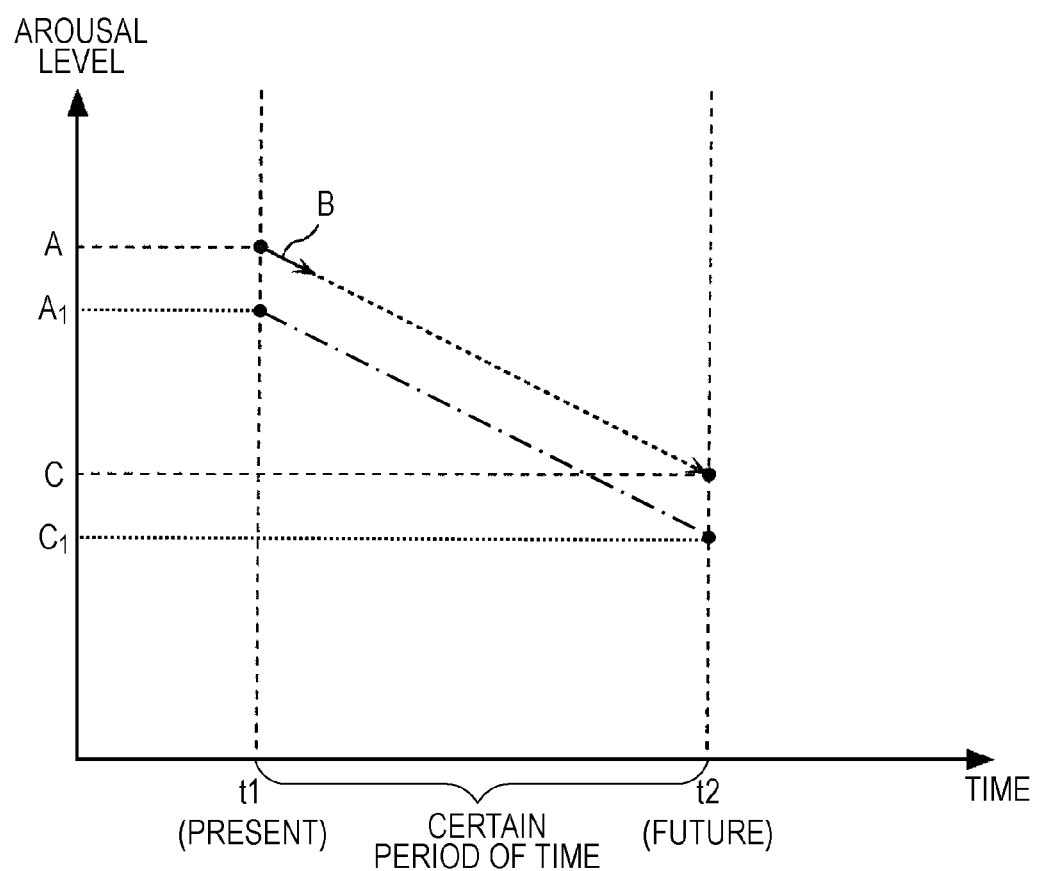
FIG. 9 is a diagram illustrating an example in which a relationship between the duration of driving and an arousal level of a driver is updated.
Figure 10:
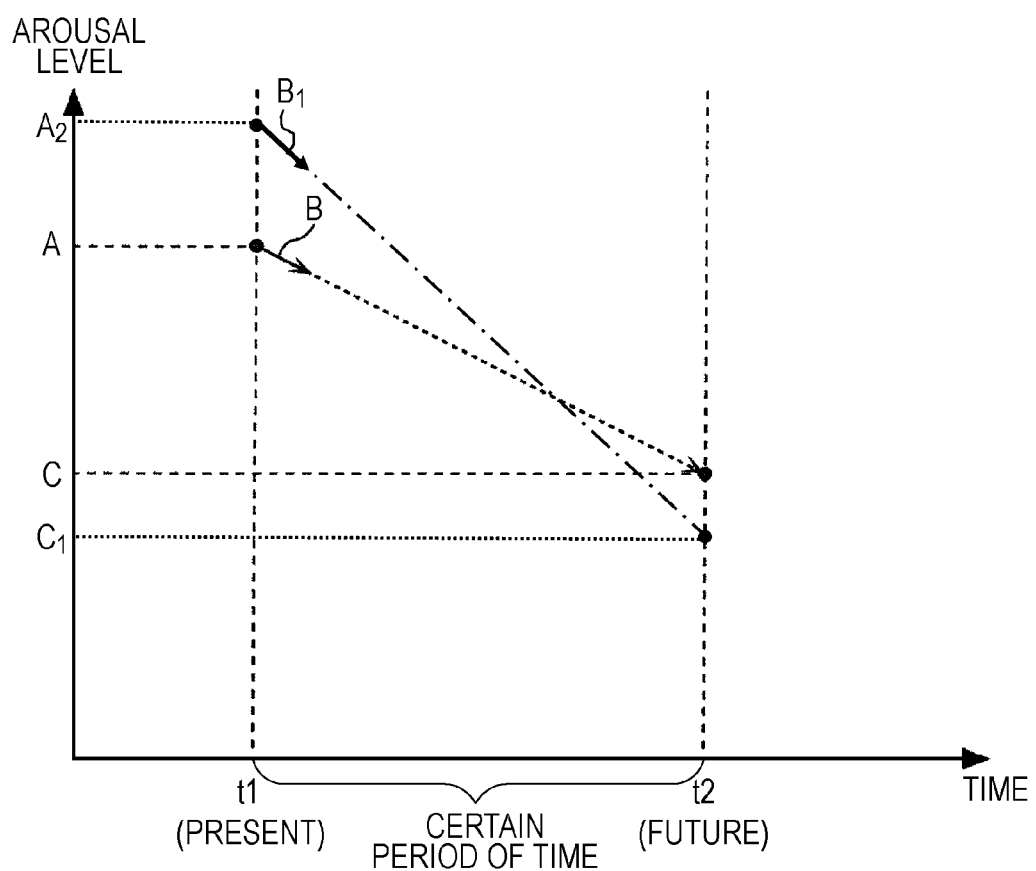
FIG. 10 is a diagram illustrating another example in which the relationship between the duration of driving and the arousal level of the driver is updated.

FIGS. 9 and 10 are diagrams illustrating examples in which a relationship between the duration of driving and the arousal level of the driver (user) is corrected.

After determining that the drowsiness level is 2, 3, or 4, for example, the processing unit 13 reads, from the memory, a relationship between time (the duration of driving) and the arousal level of the user corresponding to the environment indicated by the environment information obtained by the environment information obtaining unit 12. This relationship, for example, is the relationship indicated by a broken line in FIG. 9 or 10. In FIG. 9, a horizontal axis represents time elapsed since a beginning of driving, and a vertical axis represents the arousal level of the user. The processing unit 13 determines the arousal level of the user calculated using the biological information (e.g., the blood pressure, the heart rate, or the like) regarding the user detected when the processing unit 13 has determined that the drowsiness level is 4 as an arousal level $C_1$ at a time t2 illustrated in FIG. 9. The processing unit 13 then obtains a straight line that passes through a point identified from the time t2 and the arousal level $C_1$ and that is parallel to an arrow B. The straight line is a dash-dot line illustrated in FIG. 9.

An arousal level at a time t1 (arousal level $A_1$) is then connected to an arousal level corresponding to drowsiness level 2 or 3 using the obtained straight line, and the relationship between time (the duration of driving) and the arousal level of the user corresponding to the environment is updated as a relationship indicated by the dash-dot line illustrated in FIG. 9 and stored in the memory. The foregoing relationship may thus be updated to a relationship suitable for each user.

Alternatively, when an arousal level A2 at the time t1 is the arousal level corresponding to drowsiness level 2 or 3 calculated by the processing unit 13 and the arousal level $C_1$ at the time t2 is the arousal level corresponding to drowsiness level 4 calculated by the processing unit 13, the inclination of the arrow B illustrated in FIG. 10 may be corrected to the inclination of a straight line connecting these two actually calculated arousal levels. The straight line is a dash-dot line illustrated in FIG. 10. The straight line, which is the dash-dot line, is parallel to an arrow $B_1$ illustrated in FIG. 10. In this case, a value obtained by subtracting the time t1 from the time t2 is a time taken for drowsiness level 2 or 3 to actually change to drowsiness level 4.

The processing unit 13 may thus feed the arousal level of the user calculated using the biological information (e.g., the blood pressure, the heart rate, or the like) regarding the user detected when the processing unit 13 has detected that the drowsiness level is 4 back to correct the arousal level corresponding to drowsiness level 2, the arousal level corresponding to drowsiness level 3, or the inclination of the straight line indicated by the broken line in FIG. 10.

By performing correction in this manner, the relationship between the duration of driving and the arousal level of the user can be corrected to a relationship according to characteristics of the user.

If there are a plurality of users who drive a single automobile, the automobile or the arousal level prediction apparatus desirably includes a driver identification unit (not illustrated) that identifies a driver, and the driver identification unit desirably identifies the driver. The processing unit 13 desirably corrects the relationship indicated by the broken line in FIG. 9 or 10 to a relationship according to characteristics of the identified driver (the relationship indicated by the dash-dot line).

In doing so, drowsiness can be predicted in accordance with the characteristics of each user.

Some of the parameters (the heart rate, the LF/HF, the blood pressure, the frequency of blinks, the blink speed, and the like) used for predicting drowsiness begin to change at an initial stage of drowsiness (when the drowsiness level is low) but rates of change thereof greatly vary between individuals. The heart rate and the blood pressure are such examples. At the initial stage of drowsiness, therefore, the heart rate and the blood pressure may be used as parameters for predicting drowsiness. When a plurality of parameters are measured, the accuracy of predicting drowsiness at the initial stage of drowsiness improves, which is desirable.

On the other hand, the frequency of blinks and the blink speed hardly change at the initial stage of drowsiness (drowsiness level 1 or 2) compared to the heart rate or the like but might greatly change when the drowsiness level is high (drowsiness level 2 to 4).

After the drowsiness level becomes high (e.g., drowsiness level 3 or higher), therefore, the frequency of blinks and the blink speed may be added as parameters for predicting drowsiness.

In addition, a camera may be used for predicting drowsiness. In this case, the blink speed, a ratio of a period for which the user's eyes are open to a period for which the user's eyes are closed, and facial expressions can be measured in a noncontact manner. As a result, a plurality of parameters relating to drowsiness, such as the blink speed, the ratio of the period for which the user's eyes are open to the period for which the user's eyes are closed, the facial expressions, the heart rate, the respiration, the blood pressure, an attitude, and the LF/HF, can be measured in a noncontact manner, thereby accurately predicting drowsiness.

Although the processes in the present disclosure have been described with reference to the first and second embodiments, a subject or an apparatus that performs each process is not particularly limited. For example, the arousal level prediction apparatus may include a biological information obtaining unit, an environment information obtaining unit, a processing unit, and a control unit as described above, but may include only a processing unit and a control unit, instead. Alternatively, the processing originally performed by the arousal level prediction apparatus may be performed by a cloud server provided in a place different from a place where the local apparatus is provided, instead. For example, the cloud server and the local apparatus may share processing and control, that is, for example, the cloud server may perform heavy processing and control and the local apparatus may perform light processing and control. The cloud server and the local apparatus may be collectively referred to as an "arousal level prediction apparatus".

Alternatively, the processing originally performed by the arousal level prediction apparatus may be performed by a processor (described later) incorporated into a particular locally provided apparatus or the like, instead.

(1) The arousal level prediction apparatus is specifically a computer system including a microprocessor, a read-only memory (ROM), a random-access memory (RAM), a hard disk unit, a display unit, a keyboard, and a mouse. The RAM or the hard disk unit stores a computer program. When the microprocessor operates in accordance with the computer program, the arousal level prediction apparatus achieves the functions thereof. The computer program is a combination of a plurality of command codes for issuing instructions to a computer in order to achieve the functions.

(2) Part or all of the components of the arousal level prediction apparatus may be achieved by a single system large-scale integration (LSI) circuit. The system LSI circuit is a super-multifunctional LSI circuit fabricated by integrating a plurality of components on a single chip and, more specifically, a computer system including a microprocessor, a ROM, and a RAM. The RAM stores a computer program. When the microprocessor operates in accordance with the computer program, the system LSI circuit achieves functions thereof.

(3) Part or all of the components of the arousal level prediction apparatus may be achieved by an integrated circuit (IC) card removably attached to an apparatus or a separate module. The IC card or the module is a computer system including a microprocessor, a ROM, and a RAM. The IC card or the module may include the above-mentioned super-multifunctional LSI circuit. When the microprocessor operates in accordance with the computer program, the IC card or the module achieves functions thereof. The IC card or the module may be tamper-resistant.

(4) The present disclosure may be the above-described methods.

Alternatively, the present disclosure may be a computer program with which a computer achieves these methods, or a digital signal including the computer program.

(5) Alternatively, the present disclosure may be a computer-readable recording medium, namely, for example, a flexible disk, a hard disk, a compact disc read-only memory (CD-ROM), a magneto-optical (MO) disk, a digital versatile disc (DVD), a DVD-ROM, a DVD-RAM, a Blu-ray Disc (BD; registered trademark), or a semiconductor memory, storing the computer program or the digital signal. Alternatively, the present disclosure may be the digital signal recorded on one of these recording media.

Alternatively, the present disclosure may be the computer program or the digital signal transmitted through an electrical communication line, a wireless or wired communication line, a network typified by the Internet, datacasting, or the like.

Alternatively, the present disclosure may be a computer system including a microprocessor and a memory. The memory may store the computer program, and the microprocessor may operate in accordance with the computer program.

Alternatively, the present disclosure may be implemented by an independent computer system using the computer program or the digital signal transported in one of the recording media or through the network or the like.

(6) The above embodiments and modifications may be combined with one another.

The present disclosure is effective as a method for predicting an arousal level and an arousal level prediction apparatus that are used in a vehicle, an airplane, an office, an information terminal apparatus, or the like and that predict a future arousal level of the user.

What is claimed is:

1. A method for predicting an arousal level used by a computer of an arousal level prediction apparatus that predicts an arousal level of a user, the method comprising:
   obtaining, by a processor of the computer, current biological information regarding the user detected by a sensor;
   calculating, by the processor, a current arousal level of the user based on the current biological information;
   obtaining current environment information indicating a current environment around the user;
   predicting, by the processor, a future arousal level, which is an arousal level a certain period of time later, based on the current arousal level and the current environment information; and
   (i) issuing, by the processor, a notification to the user or (ii) controlling a first device, based on the future arousal level,
   wherein the first device is a music player installed in a same space in which the arousal level prediction apparatus is installed, and
   wherein a volume of the music player is changed when the future arousal level is lower than a certain threshold.

2. The method according to claim 1,
   wherein, in the predicting of the future arousal level, a rate of decrease in an arousal level is estimated based on how likely it is for a person to become drowsy as indicated by the current environment information, and
   wherein the future arousal level is predicted by correcting the current arousal level to the arousal level the certain period of time later using the rate of decrease.

3. The method according to claim 1,
   wherein the issuing or the controlling is performed only if the future arousal level is lower than the certain threshold.

4. The method according to claim 1,
   wherein the arousal level prediction apparatus is mounted on an automobile, and
   wherein the certain period of time is included in a time taken to arrive at a target destination, the target destination being inputted by the user to a navigation system installed in the automobile.

5. The method according to claim 1,
   wherein the biological information includes information indicating a heart rate, and
   wherein the current arousal level becomes lower as a current heart rate of the user becomes lower.

6. The method according to claim 5,
   wherein the sensor detects the current heart rate of the user using any of a milliwave sensor, a pulse oximeter, a speckle camera, and a laser Doppler velocimeter.

7. The method according to claim 1,
   wherein the biological information includes information indicating a respiratory rate or an amount of air breathed, and
   wherein the current arousal level becomes lower as a current respiratory rate of the user becomes lower or a current amount of air breathed by the user becomes smaller.

8. The method according to claim 7,
   wherein the sensor detects the current respiratory rate of the user or the current amount of air breathed by the user by measuring a change in a color of the user's skin using a photodiode.

9. The method according to claim 7,
   wherein the sensor detects the current respiratory rate of the user or the current amount of air breathed by the user by measuring a current temperature of the user's lips or a portion under the user's nose using a radiation thermometer.

10. The method according to claim 1,
    wherein the biological information includes information indicating a body surface temperature of a periphery of the user's body and a deep-body temperature of the user's body, and
    wherein the current arousal level becomes lower as a current body surface temperature of the periphery of the user's body becomes closer to the deep-body temperature of the user's body.

11. The method according to claim 1,
    wherein the biological information includes information indicating a blood flow volume in a periphery of the user's body, and
    wherein the current arousal level becomes lower as a current blood flow volume in a periphery of the user's body becomes larger.

12. The method according to claim 11,
    wherein the sensor detects the current blood flow volume in the periphery of the user's body by measuring blood flow distribution of the user using a laser speckle camera.

13. The method according to claim 2,
    wherein the current environment information includes information indicating a current illumination around the user, and
    wherein the rate of decrease in the arousal level becomes higher as the current illumination becomes lower.

14. The method according to claim 2,
    wherein the current environment information includes information indicating a current wind speed around the user, and
    wherein a higher rate of decrease in the arousal level is estimated as the current wind speed becomes lower.

15. The method according to claim 1, further comprising:
    obtaining, by the processor, sleep information indicating hours of sleep of the user of a previous day; and
    predicting, by the processor, the future arousal level based on the current arousal level, the current environment information, and the sleep information.

16. The method according to claim 1, further comprising:
    obtaining, by the processor, past sleep information indicating hours of sleep of the user in a certain period of time in past; and
    predicting, by the processor, the future arousal level based on the current arousal level, the current environment information, and the past sleep information.

17. The method according to claim 1, further comprising:
    obtaining, by the processor, information indicating an activity history of the user; and
    predicting, by the processor, the future arousal level based on the current arousal level, the current environment information, and the activity history.

18. The method according to claim 1, further comprising:
    controlling a second device, which is different from the first device, based on the future arousal level, wherein the second device is an air conditioner installed in the same space in which the arousal level prediction apparatus is installed, and wherein setting temperature or air volume of the air conditioner is changed if the future arousal level is lower than the certain threshold.

19. The method according to claim 1, further comprising:

controlling a second device, which is different from the first device, based on the future arousal level, wherein the second device is a lighting device installed in the same space in which the arousal level prediction apparatus is installed, and wherein brightness of the lighting device is increased if the future arousal level is lower than the certain threshold.

20. The method according to claim 1, further comprising:

controlling a second device, which is different from the first device, based on the future arousal level, wherein the second device is a personal computer including a display used by the user, and wherein a color or luminance of the display of the personal computer is changed if the future arousal level is lower than the certain threshold.

21. An arousal level prediction apparatus comprising:

a first sensor that detects biological information of a user;

a second sensor that detects environment information indicating an environment around the user;

a processor that calculates a current arousal level of the user based on current biological information regarding the user detected by the first sensor and that predicts a future arousal level, which is an arousal level a certain period of time later, based on the current arousal level and current environment information detected by the second sensor; and a controller that (i) issues a notification to the user or (ii) controls a first device, based on the future arousal level, wherein the first device is a music player installed in a same space in which the arousal level prediction apparatus is installed, and wherein a volume of the music player is changed when the future arousal level is lower than a certain threshold.

* * * * *

UNITED STATES PATENT AND TRADEMARK OFFICE
CERTIFICATE OF CORRECTION

PATENT NO. : 11,045,127 B2
APPLICATION NO. : 16/894202
DATED : June 29, 2021
INVENTOR(S) : Koichi Kusukame et al.

Page 1 of 1

It is certified that error appears in the above-identified patent and that said Letters Patent is hereby corrected as shown below:

On the Title Page

Column 1, Item (73), "PANASONIC INTELLECTUAL PROPERTY, Torrance, CA (US); CORPORATION OF AMERICA, Torrance, CA (US)", should be replaced with -- PANASONIC INTELLECTUAL PROPERTY CORPORATION OF AMERICA, Torrance, CA (US) --.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*